(12) United States Patent
Yerkes et al.

(10) Patent No.: US 8,883,688 B2
(45) Date of Patent: Nov. 11, 2014

(54) ARYLALKYL ESTERS OF 4-AMINO-6-(SUBSTITUTED PHENYL)-PICOLINATES AND 6-AMINO-2-(SUBSTITUTED PHENYL)-PYRIMIDINECARBOXYLATES AND THEIR USE AS SELECTIVE HERBICIDES FOR CROPS

(75) Inventors: Carla N. Yerkes, Crawfordsville, IN (US); Christian T. Lowe, Westfield, IN (US); Joseph D. Eckelbarger, Carmel, IN (US); Jeffrey B. Epp, Noblesville, IN (US); Katherine A. Guenthensperger, Daleville, IN (US); Thomas L. Siddall, Zionsville, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 153 days.

(21) Appl. No.: 13/356,668

(22) Filed: Jan. 24, 2012

(65) Prior Publication Data

US 2012/0190551 A1    Jul. 26, 2012

Related U.S. Application Data

(60) Provisional application No. 61/435,925, filed on Jan. 25, 2011.

(51) Int. Cl.
| | | |
|---|---|---|
| *C07D 213/73* | (2006.01) | |
| *C07D 213/79* | (2006.01) | |
| *A01N 43/40* | (2006.01) | |
| *C07D 239/42* | (2006.01) | |
| *C07D 239/47* | (2006.01) | |
| *C07D 405/12* | (2006.01) | |
| *A01N 43/54* | (2006.01) | |

(52) U.S. Cl.
CPC ............ *C07D 213/79* (2013.01); *C07D 213/73* (2013.01); *C07D 239/42* (2013.01); *C07D 239/47* (2013.01); *C07D 405/12* (2013.01); *A01N 43/40* (2013.01); *A01N 43/54* (2013.01)
USPC .......................................... 504/260; 546/311

(58) Field of Classification Search
CPC ...... C07D 213/73; C07D 213/79; A01N 43/40
USPC .......................................... 546/311; 504/260
See application file for complete search history.

(56) References Cited

U.S. PATENT DOCUMENTS

| | | | |
|---|---|---|---|
| 3,285,925 A | 11/1966 | Johnston et al. | |
| 3,325,272 A | 6/1967 | Hamaker | |
| 6,297,197 B1 * | 10/2001 | Fields et al. | ................... 504/260 |
| 6,784,137 B2 | 8/2004 | Balko et al. | |
| 7,300,907 B2 | 11/2007 | Epp | |
| 7,314,849 B2 | 1/2008 | Balko | |
| 7,642,220 B2 | 1/2010 | Epp | |
| 7,786,044 B2 | 8/2010 | Epp | |
| 7,863,220 B2 | 1/2011 | Clark | |
| 8,609,855 B2 * | 12/2013 | Whiteker et al. | .............. 546/310 |
| 2009/0048109 A1 | 2/2009 | Epp et al. | |
| 2009/0088322 A1 | 4/2009 | Epp et al. | |
| 2010/0041556 A1 | 2/2010 | Epp et al. | |

FOREIGN PATENT DOCUMENTS

| | | |
|---|---|---|
| WO | WO/2005/063721 A1 | 7/2005 |
| WO | WO/2007/082076 A1 | 7/2007 |

OTHER PUBLICATIONS

Ugryumov et al., CAPLUS Abstract 122:207643 (1995).*

* cited by examiner

*Primary Examiner* — Deepak Rao
(74) *Attorney, Agent, or Firm* — Michael R. Asam

(57) ABSTRACT

Arylalkyl esters of 4-aminopicolinic acids and 6-amino-4-pyrimidinecarboxylates are herbicides for control of weeds especially those species common to rice and wheat cropping systems and in pasture management programs.

11 Claims, No Drawings

ARYLALKYL ESTERS OF 4-AMINO-6-(SUBSTITUTED PHENYL)-PICOLINATES AND 6-AMINO-2-(SUBSTITUTED PHENYL)-PYRIMIDINECARBOXYLATES AND THEIR USE AS SELECTIVE HERBICIDES FOR CROPS

CROSS REFERENCE TO RELATED APPLICATIONS

This application claims the benefit of U.S. Provisional Patent Application Ser. No. 61/435,925 filed Jan. 25, 2011.

FIELD OF THE INVENTION

This invention relates to certain novel esters of 4-amino-6-(substituted phenyl)-picolinic acids and 6-amino-2-(substituted phenyl)-4-pyrimidinecarboxylic acids and to the use of these compounds as herbicides for control of weeds especially those species common to rice and wheat cropping systems and in pasture management programs.

BACKGROUND OF THE INVENTION

A number of picolinic acids and their pesticidal properties have been described in the art. U.S. Pat. Nos. 6,784,137 B2 and 7,314,849 B2 disclose a genus of 4-amino-6-arylpicolinic acids and their derivatives and their use as selective herbicides, particularly for rice and cereals such as wheat and barley. WO 2005/063721 A1, WO 2007/082076 A1, U.S. Pat. Nos. 7,863,220 B2, 7,300,907 B2, 7,642,220 B2, and 7,786,044 B2 disclose certain 6-amino-2-substituted-4-pyrimidinecarboxylic acids and their derivatives and their use as herbicides. It has now been discovered that certain esters of 4-amino-6-(substituted phenyl)picolinic acids and of 6-amino-2-(substituted phenyl)-4-pyrimidinecarboxylic acids can provide superior weed control especially in rice and wheat cropping systems and in pasture management programs.

SUMMARY OF THE INVENTION

Certain arylalkyl esters of 4-amino-6-(substituted phenyl) picolinic acids and of 6-amino-2-(substituted phenyl)-4-pyrimidinecarboxylic acids are superior herbicides with a broad spectrum of broadleaf, grass, and sedge weed control especially in rice and wheat cropping systems and in pasture management programs. The compounds further possess excellent toxicological or environmental profiles.

The invention includes compounds of Formula IA:

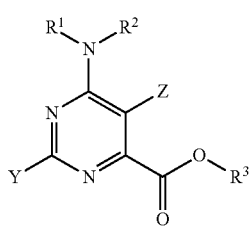

IA wherein
Y represents $C_1$-$C_8$ alkyl, $C_3$-$C_6$ cycloalkyl, or phenyl substituted with 1-4 substituents independently selected from halogen, $C_1$-$C_3$ alkyl, $C_3$-$C_6$ cycloalkyl, $C_1$-$C_3$ alkoxy, $C_1$-$C_3$ haloalkyl, $C_1$-$C_3$ haloalkoxy, cyano, nitro, $NR^1R^2$, or where two adjacent substituents are taken together as —O($CH_2$)$_n$O— or —O($CH_2$)$_n$— wherein n=1 or 2;
Z represents halogen, $C_1$-$C_3$ alkoxy, or $C_2$-$C_4$ alkenyl;
$R^1$ and $R^2$ independently represent H, $C_1$-$C_6$ alkyl, or $C_1$-$C_6$ acyl;
$R^3$ represents unsubstituted or substituted $C_7$-$C_{11}$ arylalkyl.

Preferred compounds include those in which Y represents substituted phenyl, Z represents Cl, —CH=$CH_2$ or $OCH_3$, $R^1$ and $R^2$ represent H, $R^3$ represents unsubstituted or ortho-, meta-, or para-monosubstituted benzyl.

The invention also includes compounds of Formula IB:

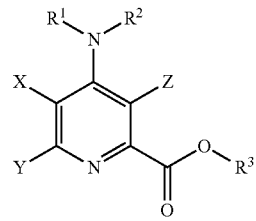

IB wherein
X=H or F;
Y represents halogen, $C_1$-$C_8$ alkyl, $C_3$-$C_6$ cycloalkyl, or phenyl substituted with 1-4 substituents independently selected from halogen, $C_1$-$C_3$ alkyl, $C_3$-$C_6$ cycloalkyl, $C_1$-$C_3$ alkoxy, $C_1$-$C_3$ haloalkyl, $C_1$-$C_3$ haloalkoxy, cyano, nitro, $NR^1R^2$, or where two adjacent substituents are taken together as —O($CH_2$)$_n$O— or —O($CH_2$)$_n$— wherein n=1 or 2;
Z represents halogen or $C_2$-$C_4$ alkenyl;
$R^1$ and $R^2$ independently represent H, $C_1$-$C_6$ alkyl, or $C_1$-$C_6$ acyl;
$R^3$ represents unsubstituted or substituted $C_7$-$C_{11}$ arylalkyl.

Preferred compounds include those in which X represents H or F, Y represents substituted phenyl, Z represents Cl, $R^1$ and $R^2$ represent H, $R^3$ represents unsubstituted or ortho-, meta-, or para-monosubstituted benzyl.

The invention includes herbicidal compositions comprising an herbicidally effective amount of a compound of Formula IA or IB in a mixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation or to the irrigation or flood water, prior to, or after emergence. The invention further includes a method for the selective postemergent control of undesirable vegetation in the presence of rice, wheat or forage, which comprises applying to said undesirable vegetation an herbicidally effective amount of a compound of the present invention. The invention also includes a method of making the compounds of the present invention.

DETAILED DESCRIPTION OF THE INVENTION

The herbicidal compounds of the present invention are arylyalkyl esters of 4-amino-6-(substituted phenyl)picolinic acids and 6-amino-2-(substituted phenyl)-4-pyrimidine-carboxylic acids and their derivatives. The picolinic acids from which the esters of Formula IB are derived are a new class of compounds having herbicidal activity. A number of picolinic acid compounds are described in U.S. Pat. Nos. 6,784,137 B2 and 7,314,849 B2, including inter alia, 4-amino-3-chloro-6-(4-chloro-2-fluoro-3-methoxy-phenyl)picolinic acid, 4-amino-3-chloro-5-fluoro-6-(4-chloro-2-fluoro-3-methoxyphenyl)picolinic acid and 4-amino-3-chloro-6-(2,4-dichloro-3-methoxyphenyl)picolinic acid. The pyrimidinecarboxylic acids from which the esters of Formula IA are derived are also a new class of compounds having herbicidal activity. A number of pyrimidinecarboxylic acid compounds are described in WO 2005/063721 A1, WO 2007/082076 A1, U.S. Pat. Nos. 7,863,220 B2, 7,300,907 B2, 7,642,220 B2, and 7,786,044 B2. These picolinic acids and pyrimidinecarboxylic acids control annual grass weeds, broadleaf weeds, and sedges in rice and wheat, but arylalkyl esters of the present invention demonstrate greater efficacy than the known esters, especially against weeds prominent in rice and wheat cropping systems and in pasture management programs.

Preferred ester groups are those which produce greater levels of weed control than an acid equivalent rate of the methyl esters. Preferred ester groups include the unsubstituted benzyl ester and ortho-, meta-, and para-monosubstituted benzyl esters.

The arylalkyl esters of the 6-amino-2-(substituted phenyl)-4-pyrimidinecarboxylic acids can be prepared by reacting the pyrimidinecarboxylic acid with an arylalkyl halide in the presence of a base.

Scheme 1

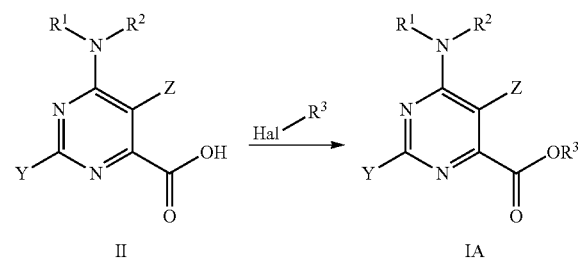

The arylalkyl esters of the picolinic acids can be prepared by coupling of picolinic acid with an alcohol using any number of suitable activating agents such as those used for peptide couplings such as dicyclohexylcarbodiimide (DCC) or carbonyl diimidazole (CDI) or by reacting the corresponding acid with an appropriate arylalkyl alcohol in the presence of an acid catalyst. Alternatively, the arylalkyl esters can be prepared by reacting the picolinic acid with an arylalkyl halide in the presence of a base.

Scheme 2

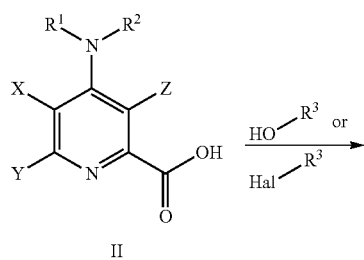

-continued

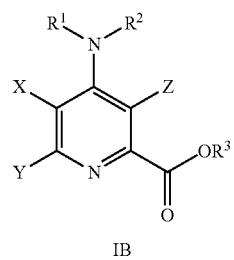

It is recognized that some reagents and reaction conditions disclosed herein or in the chemical literature for preparing compounds of Formula IA or IB may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis.

The terms "alkyl," "alkenyl" and "alkynyl," as well as derivative terms such as "alkoxy," "acyl" and "alkylthio," as used herein, include within their scope straight chain and branched chain moieties. Unless specifically stated otherwise, each may be unsubstituted or substituted with one or more substituents selected from but not limited to halogen, alkoxy, alkylthio, or aminoalkyl, provided that the substituents are sterically compatible and the rules of chemical bonding and strain energy are satisfied. The terms "alkenyl" and "alkynyl" are intended to include one or more unsaturated bonds.

The term "arylalkyl," as used herein, refers to a phenyl substituted alkyl group having a total of 7 to 11 carbon atoms, such as benzyl ($—CH_2C_6H_5$), 2-methylnaphthyl ($—CH_2C_{10}H_7$) and 1- or 2-phenethyl ($—CH_2CH_2C_6H_5$ or $—CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, $C(O)OC_1$-$C_6$alkyl, or where two adjacent substituents are taken together as $—O(CH_2)_nO—$ wherein n=1 or 2, provided that the substituents are sterically compatible and the rules of chemical bonding and strain energy are satisfied.

Unless specifically limited otherwise, the term halogen includes fluorine, chlorine, bromine, and iodine.

The compounds of Formula IA or IB have been found to be useful as pre-emergence and post-emergence herbicides for rice and cereals cropping systems and for pasture management programs. The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinating seeds, emerging seedlings, above and below ground plant parts such as shoots, roots, tubers, rhizomes and the like, and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, water quality, and the like, as well as the amount of chemical applied. These and other factors can be adjusted as is known in the art to promote selective herbicidal action. Generally, it is preferred to apply the compounds of Formula IA or IB postemergence via spray or water application to relatively immature undesirable vegetation to achieve the maximum control of weeds.

Application rates of about 1 to about 500 grams per hectare (g/ha) are generally employed in foliar-applied and water-applied postemergence operations. Preferred application rates are 10 to about 300 g/ha. For preemergence applications, rates of about 5 to about 500 g/ha are generally employed. Preferred application rates are 30 to about 300 g/ha. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: 2,4-D salts, esters and amines, acetochlor, acifluorfen, alachlor, amidosulfuron, aminopyralid, aminotriazole, ammonium thiocyanate, anilifos, atrazine, azimsulfuron, benfuresate, bensulfuron-methyl, bentazon, benthiocarb, benzobicyclon, benzofenap, bifenox, bispyribac-sodium, bromobutide, butachlor, cafenstrole, carfentrazone-ethyl, chlodinafop-propyrgyl, chlorimuron, chlorpropham, cinosulfuron, clethodim, clomazone, clomeprop, clopyralid, cloransulam-methyl, cyclosulfamuron, cycloxydim, cyhalofop-butyl, cumyluron, daimuron, diclosulam, diflufenican, diflufenzopyr, dimepiperate, dimethametryn, diquat, dithiopyr, EK2612, EPTC, esprocarb, ET-751, ethoxysulfuron, ethbenzanid, fenoxaprop, fenoxaprop-ethyl, fenoxaprop-ethyl+isoxadifen-ethyl, fentrazamide, flazasulfuron, florasulam, fluazifop, fluazifop-P-butyl, flucetosulfuron, flufenacet, flufenpyr-ethyl, flumetsulam, flumioxazin, flupyrsulfuron, fluroxypyr, fomesafen, foramsulfuron, glufosinate, glufosinate-P, glyphosate, halosulfuron-methyl, haloxyfop-methyl, haloxyfop-R, haloxyfop-R-methyl, imazamethabenz, imazamox, imazapic, imazapyr, imazaquin, imazethapyr, imazosulfuron, indanofan, ioxynil, ipfencarbazone, isoxaben, MCPA, MCPB, mefenacet, mesosulfuron, mesotrione, metamifop, metazosulfuron, metolachlor, metosulam, metsulfuron, molinate, monosulfuron, MSMA, orthosulfamuron, oryzalin, oxadiargyl, oxadiazon, oxazichlomefone, oxyfluorfen, paraquat, pendimethalin, penoxsulam, pentoxazone, pethoxamid, picloram, piperophos, pretilachlor, profoxydim, prohexadione-calcium, propachlor, propanil, propisochlor, propyzamide, propyrisulfuron, prosulfuron, pyrabuticarb, pyraclonil, pyrazogyl, pyrazolynate, pyrazosulfuron-ethyl, pyrazoxyfen, pyribenzoxim, pyridate, pyriftalid, pyriminobac-methyl, pyrimisulfan, primisulfuron, pyroxsulam, quinoclamine, quinclorac, quizalofop-P-ethyl, S-3252, sethoxydim, simazine, simetryne, s-metolachlor, sulcotrione, sulfentrazone, sulfosate, tefuryltrione, thenylchlor, thiazopyr, thiobencarb, triclopyr, triclopyr-esters and amines, trifluralin, trinexapac-ethyl, tritosulfuron, and other 4-amino-6-(substituted phenyl)picolinates and 6-amino-2-(substituted phenyl)-4-pyrimidinecarboxylates and their salts and esters.

The compounds of the present invention can additionally be employed to control undesirable vegetation in many crops that have been made tolerant to or resistant to them or to other herbicides by genetic manipulation or by mutation and selection. The herbicidal compounds of the present invention can, further, be used in conjunction with glyphosate, glufosinate, dicamba, imidazolinones, aryloxyphenoxypropionates or 2,4-D on glyphosate-tolerant, glufosinate-tolerant, dicamba-tolerant, imidazolinone-tolerant, aryloxyphenoxy-propionate tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix. Similarly the herbicidal compounds of the present invention can be used in conjunction with acetolactate synthase (ALS) inhibitors on acetolactate synthase inhibitor tolerant crops or with 4-hydroxyphenyl pyruvate dioxygenase (HPPD) inhibitors on 4-hydroxyphenyl pyruvate dioxygenase inhibitor tolerant crops.

The compounds of the present invention can generally be employed in combination with known herbicide safeners, such as benoxacor, benthiocarb, brassinolide, cloquintocet (mexyl), cyometrinil, cyprosulfamide, daimuron, dichlormid, dicyclonon, diethorate, dimepiperate, disulfoton, fenchlorazole-ethyl, fenclorim, flurazole, fluxofenim, furilazole, harpin proteins, isoxadifen-ethyl, mefenpyr-diethyl, mephenate, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugar beet, cotton, canola, and other crops that have been made tolerant or resistant to compounds that are acetolactate synthase inhibitors in sensitive plants can be treated. Many glyphosate- and glufosinate-tolerant crops can be treated as well, alone or in combination with these herbicides. Some crops have been made tolerant to auxinic herbicides and ACCase herbicides such as 2,4-(dichlorophenoxy)acetic acid (2,4-D) and dicamba and aryloxyphenoxypropionates. These herbicides may be used to treat such resistant crops or other auxin tolerant crops. Some crops have been made tolerant to 4-hydroxyphenyl pyruvate dioxygenase inhibiting herbicides, and these herbicides may be used to treat such resistant crops.

While it is possible to utilize the compounds of Formula IA or IB directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula IA or IB or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water or paddy flood water, and by other conventional means known to those skilled in the art.

The following Examples are presented to illustrate the various aspects of this invention and should not be construed as limitations to the claims.

EXAMPLES

General: Microwave heating was carried out using a Biotage Initiator™ microwave reactor. The microwave reactions were conducted in closed reaction vessels with magnetic stirring and with the temperature controlled via infrared (IR) detection.

Example 1

Preparation of benzyl 4-amino-3-chloro-6-(4-chloro-2-fluoro-3-methoxyphenyl)-5-fluoropicolinate (Compound 1)

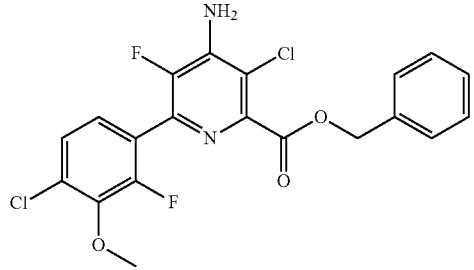 [SMILES: COc1c(Cl)ccc(-c2nc(C(=O)OCc3ccccc3)c(Cl)c(N)c2F)c1F]

To a solution of 4-amino-3-chloro-6-(4-chloro-2-fluoro-3-methoxyphenyl)-5-fluoropicolinic acid (prepared by the methods described in U.S. Pat. No. 7,314,849 B2; 100 milligrams (mg), 0.29 millimoles (mmol)) in tetrahydrofuran (THF; 1 milliliter (mL)) was added carbonyl diimidazole (51 mg, 0.32 mmol). The reaction mixture was stirred at ambient temperature for 30 minutes (min) when carbon dioxide ($CO_2$) evolution ceased. Benzyl alcohol (62 mg, 0.58 mmol) was added, and the reaction mixture was heated in a benchtop microwave at 90° C. for 20 min The reaction mixture was purified by silica gel chromatography (applied directly to an Isco 40 gram (g) RediSep® column eluting with 0-100% diethyl ether ($Et_2O$) in hexanes) to yield a white solid (147 mg, 78%): mp 132-133° C., $^1$H NMR (400 MHz, DMSO-$d_6$) δ 7.50-7.33 (m, 6H), 7.29 (dd, J=8.5, 7.1 Hz, 1H), 7.13 (s, 2H), 5.37 (s, 2H), 3.92 (s, 3H); ESIMS m/z 439 ([M+H]$^+$).

Example 2

Preparation of 4-chlorobenzyl 4-amino-3-chloro-6-(4-chloro-2-fluoro-3-methoxyphenyl)-5-fluoropicolinate (Compound 2)

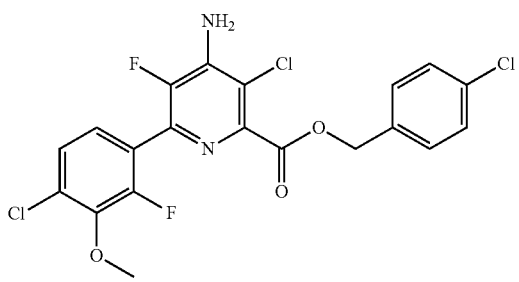 [SMILES: COc1c(Cl)ccc(-c2nc(C(=O)OCc3ccc(Cl)cc3)c(Cl)c(N)c2F)c1F]

A suspension of 4-amino-3-chloro-6-(4-chloro-2-fluoro-3-methoxyphenyl)-5-fluoropicolinic acid (150 mg, 0.43 mmol), 1-(bromomethyl)-4-methylbenzene (159 mg, 0.86 mmol), potassium carbonate ($K_2CO_3$; 118 mg, 0.86 mmol) and sodium iodide (NaI; 6 mg, 0.04 mmol) in N,N-dimethylformamide (DMF; 1 mL) was heated in a benchtop microwave at 100° C. for 5 min. The reaction mixture was then diluted with $Et_2O$, washed with brine, dried over sodium sulfate ($Na_2SO_4$) and concentrated in vacuo. The residue was purified by silica gel chromatography (eluting with a 0-70% ethyl acetate (EtOAc)/hexanes gradient) to yield a white solid (148 mg, 73%): mp 143° C.; $^1$H NMR (400 MHz, DMSO-$d_6$) δ 7.50-7.42 (m, 5H), 7.28 (dd, J=8.5, 7.1 Hz, 1H), 7.08 (s, 2H), 5.37 (s, 2H), 3.93 (d, J=0.8 Hz, 3H); ESIMS m/z 475 ([M+H]$^+$).

Compounds 3-16 in Table 1 were synthesized as in Example 2.

Example 3

Preparation of 2,4-dichlorobenzyl 4-amino-3-chloro-6-(4-chloro-2-fluoro-3-methoxyphenyl)picolinate (Compound 17)

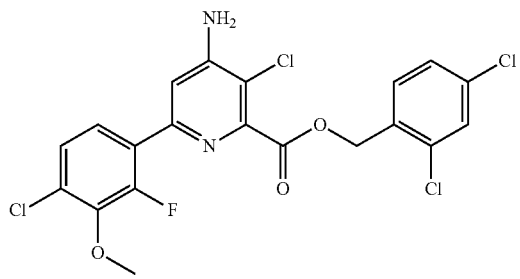 [SMILES: COc1c(Cl)ccc(-c2cc(N)c(Cl)c(C(=O)OCc3ccc(Cl)cc3Cl)n2)c1F]

4-Amino-3-chloro-6-(4-chloro-2-fluoro-3-methoxyphenyl)picolinic acid (prepared by the methods described in U.S. Pat. No. 7,314,849 B2; 828 mg, 2 5 mmol) was dissolved in DMF (4 mL). Sodium hydride (NaH, 60% disperson in mineral oil; 154 mg, 3.85 mmol) was added portion wise. To the mixture was added 2,4-dichloro-1-(chloromethyl)benzene (586 mg, 3.0 mmol). The reaction mixture was allowed to stir for 24 hours (h). Water was added to the reaction mixture, and the aqueous phase was extracted with EtOAc (×3). The combined organic extracts were washed with brine, dried with $Na_2SO_4$, filtered, and concentrated. Purification by normal phase chromatography gave a white solid (440 mg, 35%): mp 165-168° C., $^1$H NMR (400 MHz, CDCl$_3$) δ 7.68 (dd, J=8.6, 7.8 Hz, 1H), 7.54 (d, J=8.3 Hz, 1H), 7.43 (d, J=2.1 Hz, 1H), 7.28 (d, J=2.1 Hz, 1H), 7.23 (d, J=1.8 Hz, 1H), 7.21 (d, J=1.6 Hz, 1H), 5.50 (s, 2H), 4.83 (s, 2H), 3.97 (d, J=0.8 Hz, 3H); ESIMS m/z 489 ([M−H]).

Compounds 18 and 19 in Table 1 were synthesized as in Example 3.

Example 4

Preparation of 4-trifluoromethoxybenzyl 4-amino-3-chloro-6-(4-chloro-2-fluoro-3-methoxyphenyl)-5-fluoropicolinate (Compound 20)

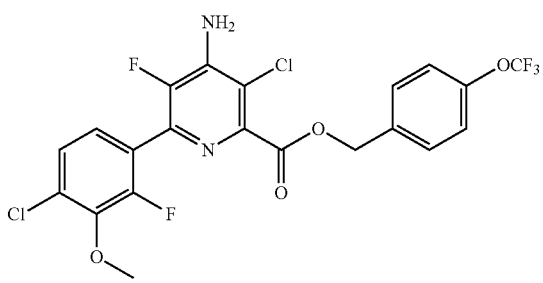 [SMILES: COc1c(Cl)ccc(-c2nc(C(=O)OCc3ccc(OC(F)(F)F)cc3)c(Cl)c(N)c2F)c1F]

A suspension of 4-amino-3-chloro-6-(4-chloro-2-fluoro-3-methoxyphenyl)-5-fluoropicolinic acid (200 mg, 0.573 mmol), 1-(bromomethyl)-4-(trifluoromethoxy)benzene (161 mg, 0.630 mmol) and $K_2CO_3$ (119 mg, 0.859 mmol) in DMF (2 mL) was heated at 50° C. overnight. The reaction mixture was then concentrated in vacuo. The residue was purified by silica gel chromatography (eluting with 0-80% EtOAc/hexane gradient) to yield a white solid (154 mg, 51.4%): mp 155-156° C.; $^1$H NMR (400 MHz, DMSO-d$_6$) δ 7.60 (d, J=8.7 Hz, 2H), 7.47 (dd, J=8.5, 1.5 Hz, 1H), 7.41 (d, J=8.0 Hz, 2H), 7.29 (dd, J=8.5, 7.1 Hz, 1H), 7.14 (s, 2H), 5.41 (s, 2H), 3.95-3.90 (m, 3H); ESIMS m/z 523 ([M+H]$^+$), 521 ([M−H]$^-$).

Compounds 21-34 in Table 1 were synthesized as in Example 4.

Example 5

Preparation of benzyl 6-amino-2-(4-chloro-2-fluoro-3-methoxyphenyl)-5-vinylpyrimidine-4-carboxylate (Compound 35)

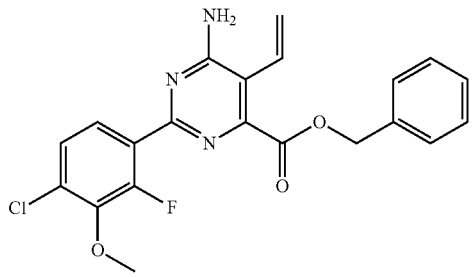 [SMILES: C=Cc1c(N)nc(-c2ccc(Cl)c(OC)c2F)nc1C(=O)OCc1ccccc1]

6-Amino-2-(4-chloro-2-fluoro-3-methoxyphenyl)-5-vinylpyrimidine-4-carboxylic acid (prepared by the methods described in U.S. Pat. No. 7,786,044 B2; 0.150 g, 0.463 mmol), (bromomethyl)benzene (0.103 g, 0.602 mmol), and lithium carbonate (Li$_2$CO$_3$; 0.044 g, 0.602 mmol) were combined in DMF (1.5 mL) and heated at 60° C. overnight. The cooled reaction mixture was concentrated and then partitioned between EtOAc and water. The organic phase was dried, concentrated and purified by column chromatography (eluting with an EtOAc/hexanes gradient) to yield benzyl 6-amino-2-(4-chloro-2-fluoro-3-methoxyphenyl)-5-vinylpyrimidine-4-carboxylate as a white solid (0.154 g, 80%): mp 119-121° C.; $^1$H NMR (400 MHz, CDCl$_3$) δ 7.67 (dd, J=8.5, 7.5 Hz, 1H), 7.49-7.42 (m, 2H), 7.42-7.32 (m, 3H), 7.21 (dd, J=8.6, 1.7 Hz, 1H), 6.70 (dd, J=17.8, 11.6 Hz, 1H), 5.60 (dd, J=7.7, 1.0 Hz, 1H), 5.57 (s, 1H), 5.39 (s, 2H), 5.35 (s, 2H), 4.00 (d, J=0.8 Hz, 3H); ESIMS m/z 414 ([M+H]$^+$).

Example 6

Preparation of 4-methoxybenzyl 4-amino-3-chloro-6-(4-chloro-2-fluoro-3-methoxyphenyl)picolinate (Compound 36)

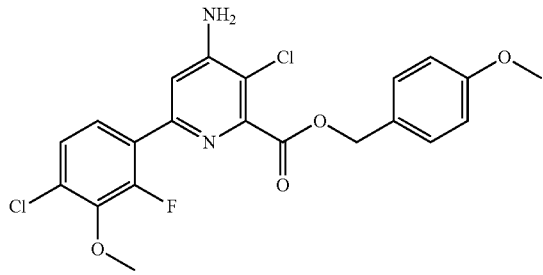 [SMILES: COc1ccc(COC(=O)c2nc(-c3ccc(Cl)c(OC)c3F)cc(N)c2Cl)cc1]

To a solution of 4-amino-3-chloro-6-(4-chloro-2-fluoro-3-methoxyphenyl)picolinic acid (600 mg, 1.81 mmol) in THF (10 mL) was added triphenylphosphine (475 mg, 1.81 mmol), diethyl azodicarboxylate (0.29 mL, 1.81 mmol), and 4-methoxybenzyl alcohol (0.34 mL, 2.72 mmol). The reaction mixture was stirred for 48 h. Additional triphenylphosphine (475 mg, 1.81 mmol) was added to the reaction, and the reaction mixture was stirred for 24 h. The reaction mixture was concentrated to dryness and was purified by silica gel chromatography (eluting with a 0-100% EtOAc/hexane gradient) to provide an off-white solid (170 mg, 26%): mp 73-83° C.; $^1$H NMR (400 MHz, CDCl$_3$) δ 7.66 (dd, J=8.6, 7.8 Hz, 1H), 7.45-7.38 (m, 2H), 7.22 (dd, J=8.7, 1.8 Hz, 1H), 7.16 (d, J=1.7 Hz, 1H), 6.94-6.87 (m, 2H), 5.38 (s, 2H), 4.80 (s, 2H), 3.96 (d, J=0.8 Hz, 3H), 3.81 (s, 3H); ESIMS m/z 451 ([M+H]$^+$), 449 ([M−H]$^-$).

Compound 37 in Table 1 was synthesized as in Example 6.

Example 7

Preparation of benzyl 4-amino-3-chloro-6-(2,4-dichloro-3-methoxyphenyl)-picolinate (Compound 38)

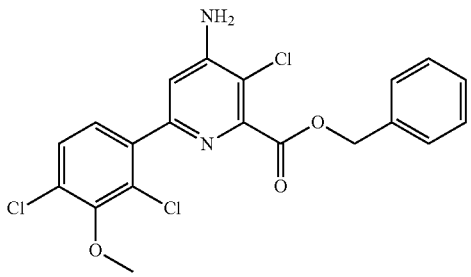 [SMILES: COc1c(Cl)ccc(-c2cc(N)c(Cl)c(C(=O)OCc3ccccc3)n2)c1Cl]

Methyl 4-amino-3-chloro-6-(2,4-dichloro-3-methoxyphenyl)picolinate (Compound C, prepared by the methods described in U.S. Pat. No. 7,314,849 B2; 500 mg, 1.4 mmol) was dissolved in benzyl alcohol (10 mL), treated with titanium(IV) isopropoxide (ca 100 μL) and heated at 85-90° C. After 2 h, another portion of titanium(IV) isopropoxide (100 μL) was added and heating was continued for another 18 h. The volatiles were removed under high vacuum, and the residue was purified by silica gel chromatography (eluting with 5% Et$_2$O-30% dichloromethane (CH$_2$Cl$_2$)-65% hexane). The material was further purified by reverse phase high performance liquid chromatography (RP-HPLC; eluting with 70% acetonitrile) to give the title compound (375 mg, 61%): mp 107-108° C.; $^1$H NMR (400 MHz, CDCl$_3$) δ 7.50-7.26 (m, 8H), 6.97 (s, 1H), 5.42 (s, 2H), 4.85 (s, 2H), 3.91 (s, 3H); ESIMS m/z 437 ([M+H]$^+$).

Compound 39 in Table 1 was synthesized as in Example 7.

Example 8

Preparation of benzyl 4-amino-3-chloro-6-(4-chloro-2-fluoro-3-(1-fluoroethyl)phenyl)-5-fluoropicolinate (Compound 40)

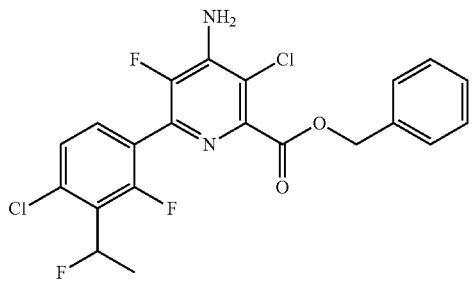 [SMILES: CC(F)c1c(Cl)ccc(-c2nc(C(=O)OCc3ccccc3)c(Cl)c(N)c2F)c1F]

Step A. Methyl 4-amino-3-chloro-6-(4-chloro-2-fluoro-3-(1-fluoroethyl)phenyl)-5-fluoropicolinate (Compound H). 2-(4-Chloro-2-fluoro-3-(1-fluoroethyl)phenyl)-4,4,5,5-tetramethyl-1,3,2-dioxaborolane (510 mg, 1.7 mmol, 1.0 equivalent (equiv)) and methyl 4-amino-3,6-dichloro-5-fluoropicolinate (prepared by the methods described in U.S. Pat. No. 6,784,137 B2; 400 mg, 1.7 mmol, 1.0 equiv) were sequentially added to a 5 mL Biotage microwave vessel, followed by cesium fluoride (CsF; 510 mg, 3.3 mmol, 2.0 equiv), palladium(II) acetate (19 mg, 0.084 mmol, 0.05 equiv), and sodium 3,3',3"-phosphinetriyltribenzenesulfonate (95 mg, 0.17 mmol, 0.10 equiv). A 3:1 mixture of water-acetonitrile (3.2 mL) was added and the resulting brown mixture was heated in a benchtop microwave at 150° C. for 5 min. The cooled reaction mixture was diluted with water (150 mL) and extracted with $CH_2Cl_2$ (4×50 mL). The combined organic extracts were dried with magnesium sulfate ($MgSO_4$), gravity filtered, and concentrated by rotary evaporation. The residue was purified by reverse phase column chromatography (eluting with a 5% acetonitrile to 100% acetonitrile gradient) to afford the desired product, methyl 4-amino-3-chloro-6-(4-chloro-2-fluoro-3-(1-fluoroethyl)phenyl)-5-fluoropicolinate as a tan semisolid (220 mg, 35%): IR (thin film) 3475 (w), 3353 (m), 3204 (w), 3001 (w), 2955 (w), 1738 (s), 1711 (s), 1624 (s) $cm^{-1}$; $^1H$ NMR (300 MHz, $CDCl_3$) δ 7.50 (m, 1H), 7.30 (m, 1H), 7.21 (d, J=2 Hz, 1H), 6.16 (dq, J=46, 7 Hz, 1H), 4.96 (br s, 2H), 3.97 (s, 3H), 1.75 (dd, J=23, 7 Hz, 3H); ESIMS m/z 379 ([M+H]$^+$).

Step B. 4-Amino-3-chloro-6-(4-chloro-2-fluoro-3-(1-fluoroethyl)phenyl)-5-fluoropicolinic acid. A 2 molar (M) solution of aqueous sodium hydroxide (NaOH; 580 μL, 1.2 mmol, 4.0 equiv) was added to a stirred suspension of methyl 4-amino-3-chloro-6-(4-chloro-2-fluoro-3-(1-fluoroethyl)phenyl)-5-fluoropicolinate (110 mg, 0.29 mmol, 1.0 equiv) in methyl alcohol (1.9 mL) at 23° C. The resulting homogeneous pale yellow solution was stirred at 23° C. for 20 h. The reaction mixture was adjusted to approximately pH=4 via dropwise addition of concentrated hydrochloric acid (HCl) and concentrated via rotary evaporation. The residue was slurried in water and vacuum filtered to afford the desired product, 4-amino-3-chloro-6-(4-chloro-2-fluoro-3-(1-fluoroethyl)phenyl)-5-fluoropicolinic acid as a white powder (55 mg, 50%): IR (thin film) 3319 (m), 3193 (w), 2983 (w), 1719 (m), 1629 (s) $cm^{-1}$; $^1H$ NMR (300 MHz, DMSO-$d_6$) δ 7.58 (t, J=9 Hz, 1H), 7.49 (d, J=9 Hz, 1H), 6.99 (br s, 2H), 6.15 (dq, J=44, 7 Hz, 1H), 1.71 (dd, J=23, 7 Hz, 3H); ESIMS m/z 365 ([M+H]$^+$).

Step C. Benzyl 4-amino-3-chloro-6-(4-chloro-2-fluoro-3-(1-fluoroethyl)phenyl)-5-fluoropicolinate. Triethylamine (190 μL, 1.4 mmol, 2.0 equiv) and benzyl bromide (120 μL, 1.0 mmol, 1.5 equiv) were sequentially added to a stirred solution of 4-amino-3-chloro-6-(4-chloro-2-fluoro-3-(1-fluoroethyl)phenyl)-5-fluoropicolinic acid (0.25 g, 0.69 mmol, 1.0 equiv) in THF (3.4 mL) at 23° C. The resulting cloudy pale yellow solution was stirred at 23° C. for 18 h. The reaction mixture was diluted with water (150 mL) and extracted with $CH_2Cl_2$ (3×70 mL). The combined organic layers were dried ($MgSO_4$), gravity filtered, and concentrated by rotary evaporation. The residue was purified by reverse phase column chromatography (eluting with a 5% acetonitrile to 100% acetonitrile gradient) to afford the desired product, benzyl 4-amino-3-chloro-6-(4-chloro-2-fluoro-3-(1-fluoroethyl)phenyl)-5-fluoropicolinate as a yellow semisolid (160 mg, 52%): IR (thin film) 3485 (m), 3393 (m), 3196 (w), 3035 (w), 2983 (w), 1737 (s), 1622 (s) $cm^{-1}$; $^1H$ NMR (300 MHz, $CDCl_3$) δ 7.23-7.57 (m, 7H), 6.18 (dq, J=45, 6 Hz, 1H), 5.45 (s, 2H), 4.94 (br s, 2H), 1.78 (ddd, J=23, 7, 1 Hz, 3H); ESIMS m/z 453 ([M+H]$^+$).

Example 9

Preparation of benzyl 4-amino-3-chloro-6-(4-chloro-3-ethoxy-2-fluorophenyl)-5-fluoropicolinate (Compound 41)

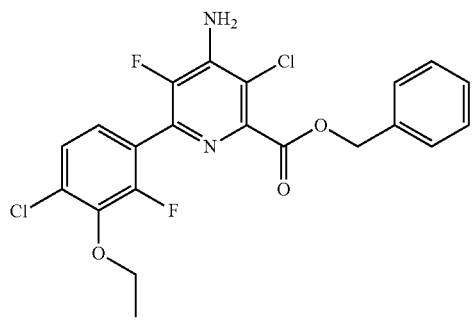 [SMILES: CCOc1c(Cl)ccc(-c2nc(C(=O)OCc3ccccc3)c(Cl)c(N)c2F)c1F]

Step A. Methyl 4-amino-3-chloro-6-(4-chloro-3-ethoxy-2-fluorophenyl)-5-fluoropicolinate (Compound A). 2-(4-Chloro-3-ethoxy-2-fluorophenyl)-4,4,5,5-tetramethyl-1,3,2-dioxaborolane (500 mg, 1.7 mmol, 1.0 equiv) and methyl 4-amino-3,6-dichloro-5-fluoropicolinate (400 mg, 1.7 mmol, 1.0 equiv) were sequentially added to a 5 mL Biotage microwave vessel, followed by CsF (510 mg, 3.3 mmol, 2.0 equiv), palladium(II) acetate (19 mg, 0.084 mmol, 0.05 equiv), and sodium 3,3',3"-phosphinetriyltribenzene-sulfonate (95 mg, 0.17 mmol, 0.10 equiv). A 3:1 mixture of water-acetonitrile (3.2 mL) was added, and the resulting brown mixture was heated in a benchtop microwave at 150° C. for 5 min. The cooled reaction mixture was diluted with water (150 mL) and extracted with $CH_2Cl_2$ (4×50 mL). The combined organic extracts were dried ($MgSO_4$), gravity filtered, and concentrated by rotary evaporation. The residue was purified by silica gel column chromatography (eluting with 33% EtOAc/hexane) to afford the desired product, methyl 4-amino-3-chloro-6-(4-chloro-3-ethoxy-2-fluorophenyl)-5-fluoropicolinate as a tan powder (450 mg, 63%): mp 170-172° C.; IR (thin film) 3485 (m), 3380 (s), 2951 (w), 1739 (s), 1610 (s) $cm^{-1}$; $^1H$ NMR (300 MHz, $CDCl_3$) δ 7.20-7.30 (m, 2H), 4.95 (br s, 2H), 4.19 (q, J=7 Hz, 2H), 3.98 (s, 3H), 1.43 (t, J=7 Hz, 3H); ESIMS m/z 377 ([M+H]$^+$).

Step B. 4-Amino-3-chloro-6-(4-chloro-3-ethoxy-2-fluorophenyl)-5-fluoropicolinic acid. A 2 M solution of aqueous NaOH (900 μL, 1.8 mmol, 4.0 equiv) was added to a stirred suspension of methyl 4-amino-3-chloro-6-(4-chloro-3-ethoxy-2-fluorophenyl)-5-fluoropicolinate (170 mg, 0.45 mmol, 1.0 equiv) in methyl alcohol (3.0 mL) at 23° C. The resulting heterogeneous white mixture was stirred at 23° C. for 4 h. The reaction mixture was adjusted to approximately pH=4 via dropwise addition of concentrated HCl and then concentrated via rotary evaporation. The residue was slurried in water and vacuum filtered to afford the desired product, 4-amino-3-chloro-6-(4-chloro-3-ethoxy-2-fluorophenyl)-5-fluoropicolinic acid as a white powder (140 mg, 88%): mp 163-165° C.; IR (thin film) 3486 (m), 3377 (s), 3155 (w), 2981 (w), 2935 (w), 1718 (s), 1614 (s) cm$^{-1}$; $^1$H NMR (300 MHz, DMSO-d$_6$) δ 7.45 (dd, J=9, 2 Hz, 1H), 7.28 (dd, J=9, 7 Hz, 1H), 7.01 (br s, 2H), 4.15 (q, J=7 Hz, 2H), 1.33 (t, J=7 Hz, 3H); ESIMS m/z 363 ([M+H]$^+$).

Step C. Benzyl 4-amino-3-chloro-6-(4-chloro-3-ethoxy-2-fluorophenyl)-5-fluoropicolinate. Triethylamine (290 μL, 2.1 mmol, 2.0 equiv) and benzyl bromide (190 μL, 1.6 mmol, 1.5 equiv) were sequentially added to a stirred solution of 4-amino-3-chloro-6-(4-chloro-3-ethoxy-2-fluorophenyl)-5-fluoropicolinic acid (0.38 g, 1.1 mmol, 1.0 equiv) in THF (7.0 mL) at 23° C. The resulting cloudy brown solution was stirred at 23° C. for 18 h. The reaction mixture was diluted with water (150 mL) and extracted with CH$_2$Cl$_2$ (3×70 mL). The combined organic extracts were dried (MgSO$_4$), gravity filtered, and concentrated by rotary evaporation. The residue was purified by RP-HPLC (eluting with a 5% acetonitrile to 100% acetonitrile gradient) to afford the desired product, benzyl 4-amino-3-chloro-6-(4-chloro-3-ethoxy-2-fluorophenyl)-5-fluoropicolinate as a white powder (230 mg, 49%): mp 122-124° C.; IR (thin film) 3477 (s), 3372 (s), 3194 (w), 3036 (w), 2992 (m), 2943 (w), 2900 (w), 1729 (s), 1616 (s) cm$^{-1}$; $^1$H NMR (300 MHz, CDCl$_3$) δ 7.49-7.32 (m, 5H), 7.29-7.21 (m, 2H), 5.43 (s, 2H), 4.91 (br s, 2H), 4.19 (q, J=7 Hz, 2H), 1.43 (t, J=7 Hz, 3H); ESIMS m/z 453 ([M+H]$^+$).

Example 10

Preparation of benzyl 4-amino-3-chloro-6-(4-cyclopropylphenyl)-5-fluoropicolinate (Compound 42)

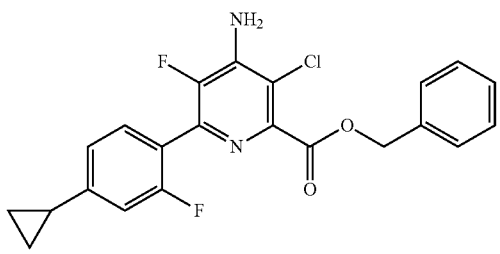 [SMILES: Nc1c(F)c(-c2ccc(C3CC3)cc2F)nc(C(=O)OCc2ccccc2)c1Cl]

Step A. Ethyl 4-amino-3-chloro-6-(4-cyclopropylphenyl)-5-fluoropicolinate. 4-Cyclopropylphenylboronic acid (250 mg, 1.5 mmol, 1.2 equiv) and methyl 4-amino-3,6-dichloro-5-fluoropicolinate (300 mg, 1.3 mmol, 1.0 equiv) were sequentially added to a 5 mL Biotage microwave vessel, followed by CsF (380 mg, 2.5 mmol, 2.0 equiv), palladium (II) acetate (14 mg, 0.063 mmol, 0.05 equiv), and sodium 3,3',3"-phosphinetriyl-tribenzenesulfonate (71 mg, 0.13 mmol, 0.10 equiv). A 3:1 mixture of water-acetonitrile (2.5 mL) was added, and the resulting brown mixture was heated in a benchtop microwave at 150° C. for 5 min. The cooled reaction mixture was diluted with water (150 mL) and extracted with CH$_2$Cl$_2$ (4×50 mL). The combined organic extracts were dried (MgSO$_4$), gravity filtered, and concentrated by rotary evaporation. The residue was purified by RP-HPLC (eluting with a 5% acetonitrile to 100% acetonitrile gradient) to afford the desired product, methyl 4-amino-3-chloro-6-(4-cyclopropylphenyl)-5-fluoropicolinate as a white powder (310 mg, 78%): mp 116-119° C.; IR (thin film) 3475 (s), 3357 (s), 3089 (w), 3013 (w), 2954 (w), 1724 (m), 1607 (m) cm$^{-1}$; $^1$H NMR (300 MHz, CDCl$_3$) δ 7.81 (m, 2H), 7.15 (m, 2H), 4.85 (br s, 2H), 3.98 (s, 3H), 1.94 (m, 1H), 1.01 (m, 2H), 0.74 (m, 2H); ESIMS m/z 321 ([M+H]$^+$).

Step B. 4-Amino-3-chloro-6-(4-cyclopropylphenyl)-5-fluoropicolinic acid. A 2 M solution of aqueous NaOH (600 μL, 1.2 mmol, 2.0 equiv) was added to a stirred suspension of methyl 4-amino-3-chloro-6-(4-cyclopropylphenyl)-5-fluoropicolinate (190 mg, 0.59 mmol, 1.0 equiv) in methyl alcohol (3.0 mL) at 23° C. The resulting heterogeneous white mixture was stirred at 23° C. for 3 h. The reaction mixture was adjusted to approximately pH=4 via dropwise addition of concentrated HCl and then concentrated via rotary evaporation. The residue was slurried in water and vacuum filtered to afford the desired product, 4-amino-3-chloro-6-(4-cyclopropylphenyl)-5-fluoropicolinic acid as a white powder (170 mg, 94% yield): mp 147-149° C.; IR (thin film) 3463 (s), 3339 (s), 3202 (m), 3084 (w), 3007 (w), 1721 (m), 1630 (s) cm$^{-1}$; $^1$H NMR (300 MHz, DMSO-d$_6$) δ 7.70 (m, 2H), 7.17 (m, 2H), 6.81 (br s, 2H), 1.96 (m, 1H), 0.99 (m, 2H), 0.71 (m, 2H); ESIMS m/z 307 ([M+H]$^+$).

Step C. Benzyl 4-amino-3-chloro-6-(4-cyclopropylphenyl)-5-fluoropicolinate. Triethylamine (220 μL, 1.6 mmol, 2.0 equiv) and benzyl bromide (140 μL, 1.2 mmol, 1.5 equiv) were sequentially added to a stirred solution of 4-amino-3-chloro-6-(4-chloro-3-ethoxy-2-fluorophenyl)-5-fluoropicolinic acid (0.24 g, 0.78 mmol, 1.0 equiv) in THF (5.2 mL) at 23° C. The resulting cloudy pale yellow solution was stirred at 23° C. for 72 h. The reaction mixture was diluted with water (150 mL) and extracted with CH$_2$Cl$_2$ (3×70 mL). The combined organic extracts were dried (MgSO$_4$), gravity filtered, and concentrated by rotary evaporation. The residue was purified by RP-HPLC (eluting with a 5% acetonitrile to 100% acetonitrile gradient) to afford the desired product, benzyl 4-amino-3-chloro-6-(4-cyclopropylphenyl)-5-fluoropicolinate as a white powder (180 mg, 58%): mp 129-131° C.; IR (thin film) 3389 (s), 3229 (w), 3194 (w), 3083 (w), 3068 (w), 3033 (w), 3008 (w), 1737 (s), 1616 (s) cm$^{-1}$; $^1$H NMR (300 MHz, CDCl$_3$) δ 7.83 (m, 2H), 7.48 (m, 2H), 7.33-7.42 (m, 3H), 7.15 (m, 2H), 5.43 (s, 2H), 4.82 (br s, 2H), 1.94 (m, 1H), 1.01 (m, 2H), 0.75 (m, 2H); ESIMS m/z 497 ([M+H]$^+$).

Example 11

Preparation of benzyl 4-amino-3-bromo-6-(4-chloro-2-fluoro-3-methoxy-phenyl)-5-fluoropicolinate (Compound 43)

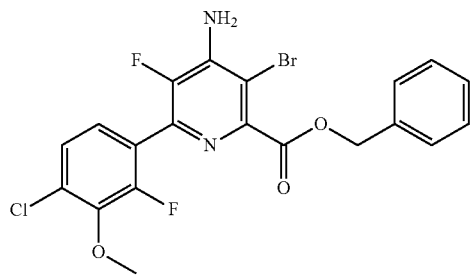 [SMILES: COc1c(Cl)ccc(-c2nc(C(=O)OCc3ccccc3)c(Br)c(N)c2F)c1F]

Step A. A mixture of methyl 4,5,6-trichloropicolinate (prepared by the methods described in U.S. Pat. No. 6,784,137 B2; 25 g, 0.10 moles (mol)) and benzyl alcohol (100 g, 0.2 mol) in a 250 mL three-neck round bottom flask was heated under nitrogen at 100° C. Titanium isopropoxide (0.6 g, 0.02 mol) was added. After 4 h at 100° C., the nearly colorless solution was cooled and transferred to a 250 mL round bottom single neck flask. Excess benzyl alcohol was removed under vacuum to give a nearly white solid (31 g, 94%): mp 125-126.5° C.; $^1$H NMR (400 MHz, CDCl$_3$) δ 8.08 (s, 1H, pyridine H), 7.42 (m, 2H, phenyl), 7.31 (m, 3H, phenyl), 5.40 (s, 2H, CH$_2$Ph); $^{13}$C{$^1$H} NMR (101 MHz, CDCl$_3$) δ 162.0 (CO$_2$R), 150.4, 145.0, 144.9, 134.7, 133.1, 128.3 (phenyl CH), 125.4 (pyridine CH), 67.88 (CH$_2$Ph).

Step B. A 250 mL three-neck flask equipped with a reflux condenser and nitrogen (N$_2$) inlet was charged with benzyl 4,5,6-trichloropicolinate (17.77 g, 56.10 mmol), 2-(4-chloro-2-fluoro-3-methoxyphenyl)-1,3,2-dioxaborinane (19.20 g, 79.0 mmol) and CsF (17.04 g, 112.0 mmol). Acetonitrile (100 mL) and water (30 mL) were added. The reaction mixture was evacuated/backfilled with N$_2$ (5×). Solid dichlorobis(triphenylphosphine)palladium(II) (Pd(PPh$_3$)$_2$Cl$_2$; 1.724 g, 2.456 mmol) was added. The solution was evacuated/backfilled with N$_2$ (5×) and then stirred at reflux for 90 min. A white solid precipitated upon cooling to room temperature. The solid was filtered, washed with water and dried in air (18.66 g, 75%): $^1$H NMR (400 MHz, CDCl$_3$) δ 8.23 (s, 1H, pyridine H), 7.52-7.32 (m, 5H, phenyl), 7.27 (dd, $J_{H-H}$=8.4 Hz, $J_{F-H}$=1.7 Hz, 1H, aromatic), 7.10 (dd, $J_{H-H}$=8.4 Hz, $J_{F-H}$=6.8 Hz, 1H, aromatic), 5.44 (s, 2H, CH$_2$Ph), 3.98 (d, $J_{F-H}$=1.3 Hz, 3H, OMe); $^{13}$C{$^1$H} NMR (101 MHz, CDCl$_3$) δ 163.0, 153.7, 153.5 (d, $J_{F-C}$=253 Hz, C2'), 146.0, 144.5 (d, $J_{F-C}$=13 Hz), 144.1, 135.0, 134.2, 129.9 (d, $J_{F-C}$=3 Hz), 128.5, 126.1, 125.8 (d, $J_{F-C}$=14 Hz), 125.3 (d, $J_{F-C}$=3 Hz), 124.9 (d, $J_{F-C}$=2 Hz), 67.9 (CH$_2$), 61.5 (d, $J_{F-C}$=4 Hz, OMe). Anal. Calcd for C$_{20}$H$_{13}$Cl$_3$FNO$_3$: C, 54.51; H, 2.97; N, 3.18. Found: C, 54.60; H, 3.08; N, 3.16.

Step C. A 250 mL three-neck flask was equipped with a distillation head, a N$_2$ inlet, a mechanical stirrer and a thermocouple. The flask was charged with CsF (21.07 g, 139.0 mmol). Anhydrous DMSO (100 mL) was added, and the suspension was evacuated/backfilled (5×) with N$_2$. The suspension was heated at 80° C. for 30 min. DMSO (30 mL) was distilled off under vacuum to remove any residual water. Solid benzyl 4,5-dichloro-6-(4-chloro-2-fluoro-3-methoxyphenyl) picolinate (15.34 g, 34.8 mmol) was added, and the solution was evacuated/backfilled with N$_2$ (5×). The reaction mixture was heated to 105° C. under N$_2$. After 6 h at 105° C., analysis of an aliquot by GC showed no peak for the monofluoro intermediate. The reaction mixture was allowed to cool to room temperature. The reaction mixture was poured into ice-water (400 g) and was extracted with EtOAc (3×200 mL). The combined organic extracts were washed with saturated (satd) NaHCO$_3$ solution, water (5×100 mL) and brine. The extracts were dried (MgSO$_4$) and concentrated under reduced pressure to give a tan solid (12.97 g). The solid was purified by flash chromatography (330 g silica column; 0-20% EtOAc-gradient) to give a white solid (9.95 g; 70%): mp 114-116° C.; $^1$H NMR (400 MHz, CDCl$_3$) δ 8.01 (dd, $J_{F-H}$=9.4, 5.5 Hz, 1H, Pyridine H), 7.53-7.20 (m, 7H, phenyl), 5.44 (s, 2H, CH$_2$Ph), 3.99 (d, $J_{F-H}$=1.2 Hz, 3H, OMe); $^{13}$C NMR (101 MHz, CDCl$_3$) δ 162.8 (d, $J_{F-C}$=3 Hz, CO$_2$Bn), 156.2 (dd, $J_{F-C}$=267, 12 Hz), 153.9 (d, $J_{F-C}$=255 Hz), 148.0 (dd, $J_{F-C}$=269, 11 Hz), 145.4 (t, $J_{F-C}$=7 Hz), 144.7 (d, $J_{F-C}$=13 Hz), 144.6 (dd, $J_{F-C}$=13, 2 Hz), 135.2 (s), 130.6 (d, $J_{F-C}$=3 Hz), 125.6 (d, $J_{F-C}$=4 Hz), 125.4 (d, $J_{F-C}$=2 Hz), 122.0 (d, $J_{F-C}$=14 Hz), 115.0 (d, $J_{F-C}$=16 Hz), 67.9 (s, CH$_2$Ph), 61.6 (d, $J_{F-C}$=5 Hz, OMe); $^{19}$F{$^1$H} NMR (376 MHz, CDCl$_3$) δ −123.90 (d, $J_{F-F}$=19.7 Hz, F4), −128.37 (d, $J_{F-F}$=33.5 Hz, F2'), −139.64 (dd, $J_{F-F}$=33.5, 19.7 Hz, F5). Anal. Calcd for C$_{20}$H$_{13}$ClF$_3$NO$_3$: C, 58.91; H, 3.21; N, 3.43. Found: C, 59.03; H, 3.20; N, 3.39.

Step D. Benzyl 4,5-difluoro-6-(4-chloro-2-fluoro-3-methoxyphenyl)picolinate (4.99 g, 12.2 mmol) was slurried in DMSO (100 mL) Ammonia was bubbled through the solution for 30 min. After stirring overnight, the reaction mixture was poured into ice-water (500 mL). The product was extracted into EtOAc (3×150 mL). The combined organic extracts were washed with water (5×100 mL) and brine, dried (MgSO$_4$) and concentrated under reduced pressure to give a white solid (4.99 g, 101%); $^1$H NMR (400 MHz, CDCl$_3$) δ 7.52 (d, $J_{F-H}$=6.5 Hz, 1H, pyridine H3), 7.45-7.38 (m, 2H), 7.37-7.17 (m, 5H), 5.38 (s, 2H, CH$_2$Ph), 4.67 (br s, 2H, NH$_2$), 3.94 (d, $J_{F-H}$=1.1 Hz, 3H, OMe); $^{13}$C{$^1$H} NMR (101 MHz, CDCl$_3$) δ 164.4 (CO$_2$R), 153.9 (d, $J_{F-C}$=254 Hz), 147.6 (d, $J_{F-C}$=256 Hz), 144.4 (d, $J_{F-C}$=14 Hz), 144.0 (d, $J_{F-C}$=5 Hz), 142.2 (d, $J_{F-C}$=12 Hz), 140.4 (d, $J_{F-C}$=15 Hz), 135.6 (s), 129.5 (d, $J_{F-C}$=3 Hz), 128.5 (CH), 128.3 (CH), 128.3 (CH), 125.6 (d, $J_{F-C}$=3 Hz, CH), 125.2 (d, $J_{F-C}$=4 Hz, CH), 123.3 (dd, $J_{F-C}$=14, 4 Hz), 113.1 (d, $J_{F-C}$=4 Hz, C3), 67.3 (s, CH$_2$Ph), 61.5 (d, $J_{F-C}$=4 Hz, OMe); $^{19}$F{$^1$H} NMR (376 MHz, CDCl$_3$) δ −128.54 (dd, J=30.7, 5.2 Hz, F2'), −141.84 (dd, J=30.8, 6.5 Hz, F5). HRMS-ESI (m/z) [M]$^+$ calcd for C$_{20}$H$_{15}$ClF$_2$N$_2$O$_3$, 404.0739; found, 404.0757.

Step E. N-Bromosuccinimide (NBS; 580 mg, 3.3 mmol, 1.1 equiv) was added to a stirred suspension of benzyl 4-amino-6-(4-chloro-2-fluoro-3-methoxyphenyl)-5-fluoropicolinate (1.2 g, 3.0 mmol, 1.0 equiv) in 1,2-dichloroethane (15 mL) at 23° C. The resulting bright yellow mixture was stirred at 23° C. for 72 h. The brown reaction mixture was concentrated by N$_2$ stream and the residue was purified by silica gel column chromatography (eluting with 29% EtOAc/hexane) to afford the desired product, benzyl 4-amino-3-bromo-6-(4-chloro-2-fluoro-3-methoxyphenyl)-5-fluoropicolinate as a tan powder (1.3 g, 93%): mp 144-146° C.; IR (thin film) 3370 (s), 3225 (w), 3190 (w), 3093 (w), 3066 (w), 3037 (w), 2948 (w), 1731 (s), 1616 (s) cm$^{-1}$; $^1$H NMR (400 MHz, CDCl$_3$) δ 7.47 (m, 2H), 7.41-7.33 (m, 3H), 7.26-7.22 (m, 2H), 5.42 (s, 2H), 4.98 (br s, 2H), 3.96 (d, J=1 Hz, 3H); ESIMS m/z 485 ([M+H]$^+$).

Example 12

Preparation of (E)-benzyl 4-amino-6-(4-chloro-2-fluoro-3-methoxy-phenyl)-3-(2-chlorovinyl)-5-fluoropicolinate (Compound 44)

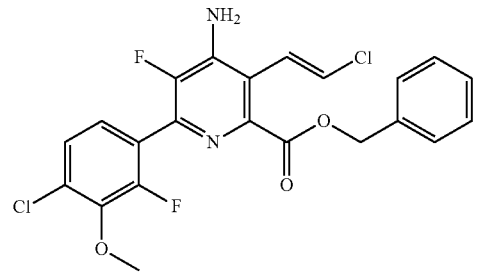 [SMILES: COc1c(Cl)ccc(-c2nc(C(=O)OCc3ccccc3)c(/C=C/Cl)c(N)c2F)c1F]

Step A. Tributyltin hydride (2.0 mL, 7.3 mmol, 1.0 equiv) and ethynyltrimethylsilane (2.1 mL, 15 mmol, 2.0 equiv) were combined, 2,2'-azobis(2-methylpropionitrile) (AIBN; 60 mg, 0.36 mmol, 0.05 equiv) was added, and the resulting colorless neat solution was heated to 80° C. Upon heating, an exothermed to ~110° C. was observed. The reaction mixture was cooled back to 80° C. and stirred for 20 h. The reaction mixture was cooled to 23° C. to afford the crude desired product, (E)-trimethyl(2-(tributylstannyl)vinyl)silane, as a pale yellow oil (2.8 g, 99% crude yield): $^1$H NMR (400 MHz, CDCl$_3$) δ 6.96 (d, J=22.5 Hz, 1H), 6.60 (d, J=22.5 Hz, 1H), 1.54-1.44 (m, 6H), 1.35-1.23 (m, 6H), 0.91-0.82 (m, 15H), 0.03 (s, 9H).

Step B. (E)-Trimethyl(2-(tributylstannyl)vinyl)silane (1.1 g, 2.7 mmol, 1.1 equiv) was added to a stirred mixture of benzyl 4-amino-3-bromo-6-(4-chloro-2-fluoro-3-methoxyphenyl)-5-fluoropicolinate (Compound 43; 1.2 g, 2.5 mmol, 1.0 equiv) and tetrakis(triphenylphosphine)palladium(0) (290 mg, 0.25 mmol, 0.10 equiv) in DMF (8.3 mL) at 23° C. The reaction mixture was heated to 90° C., resulting in a homogeneous dark yellow solution, and the reaction mixture was stirred for 20 h. The cooled reaction mixture was diluted with water (400 mL) and extracted with Et$_2$O (4×100 mL). The organic layer was dried (MgSO$_4$), gravity filtered, and concentrated by rotary evaporation. The residue was purified by reverse phase column chromatography (5% acetonitrile to 100% acetonitrile gradient) to afford the desired product, (E)-benzyl 4-amino-6-(4-chloro-2-fluoro-3-methoxyphenyl)-5-fluoro-3-(2-(trimethylsilyl)vinyl)picolinate, as a light brown oil (460 mg, 38%): IR (thin film) 3483 (w), 3376 (m), 3206 (w), 3069 (w), 2955 (s), 2897 (w), 1732 (s), 1619 (s) cm$^{-1}$; $^1$H NMR (400 MHz, CDCl$_3$) δ 7.44-7.27 (m, 7H), 6.94 (d, J=20 Hz, 1H), 6.28 (d, J=20 Hz, 1H), 5.33 (s, 2H), 4.62 (br s, 2H), 3.95 (d, J=1 Hz, 3H), 0.09 (s, 9H); ESIMS m/z 503 ([M+H]$^+$).

Step C. N-Chlorosuccinimide (NCS; 190 mg, 1.4 mmol, 2.0 equiv) was added to a stirred solution of (E)-benzyl 4-amino-6-(4-chloro-2-fluoro-3-methoxyphenyl)-5-fluoro-3-(2-(trimethylsilyl)vinyl)picolinate (350 mg, 0.70 mmol, 1.0 equiv) in DMF (7.0 mL) at 23° C. The homogeneous pale green solution was heated to 50° C. and stirred for 24 h. The cooled reaction mixture was diluted with water (400 mL) and extracted with Et$_2$O (4×100 mL).

The combined organic layers were dried (MgSO$_4$), gravity filtered, and concentrated by rotary evaporation. The residue was purified by reverse phase column chromatography (5% acetonitrile to 100% acetonitrile gradient) to afford the desired product, (E)-benzyl 4-amino-6-(4-chloro-2-fluoro-3-methoxyphenyl)-3-(2-chlorovinyl)-5-fluoropicolinate as a tan powder (70 mg, 22% yield): mp 133-135° C.; IR (thin film) 3486 (s), 3345 (s), 3215 (w), 3069 (w), 3037 (w), 2953 (w), 1719 (s), 1616 (s) cm$^{-1}$; $^1$H NMR (400 MHz, CDCl$_3$) δ 7.47-7.43 (m, 2H), 7.41-7.33 (m, 3H), 7.27 (m, 2H), 6.89 (d, J=14 Hz, 1H), 6.45 (d, J=14 Hz, 1H), 5.37 (s, 2H), 4.62 (br s, 2H), 3.97 (d, J=1 Hz, 3H); ESIMS m/z 465 ([M+H]$^+$).

TABLE 1

Structures of Compounds in Examples

| Compound Number | Structure |
|---|---|
| 3 | 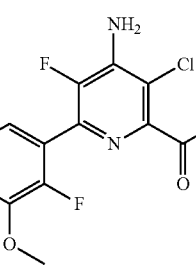 |
| 4 | 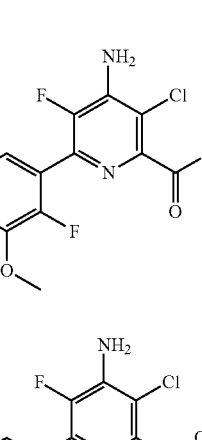 |
| 5 | 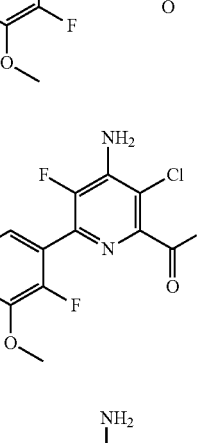 |
| 6 | 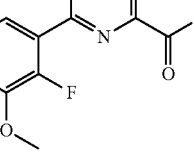 |
| 7 | 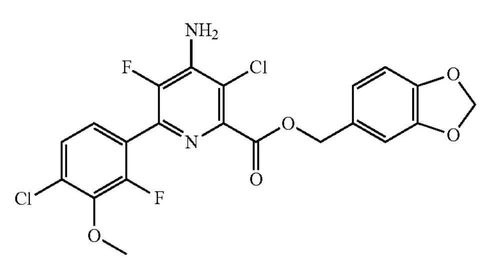 [SMILES: COc1c(Cl)ccc(-c2nc(C(=O)OCc3ccc4c(c3)OCO4)c(Cl)c(N)c2F)c1F] |

TABLE 1-continued

Structures of Compounds in Examples

| Compound Number | Structure |
| --- | --- |
| 8 | 2-methylbenzyl 4-amino-3-chloro-6-(4-chloro-2-fluoro-3-methoxyphenyl)-5-fluoropicolinate |
| 9 | 2-chlorobenzyl 4-amino-3-chloro-6-(4-chloro-2-fluoro-3-methoxyphenyl)-5-fluoropicolinate |
| 10 | 2-methoxybenzyl 4-amino-3-chloro-6-(4-chloro-2-fluoro-3-methoxyphenyl)-5-fluoropicolinate |
| 11 | 3-methylbenzyl 4-amino-3-chloro-6-(4-chloro-2-fluoro-3-methoxyphenyl)-5-fluoropicolinate |
| 12 | 3-chlorobenzyl 4-amino-3-chloro-6-(4-chloro-2-fluoro-3-methoxyphenyl)-5-fluoropicolinate |
| 13 | 3-methoxybenzyl 4-amino-3-chloro-6-(4-chloro-2-fluoro-3-methoxyphenyl)-5-fluoropicolinate |
| 14 | 1-phenylethyl 4-amino-3-chloro-6-(4-chloro-2-fluoro-3-methoxyphenyl)-5-fluoropicolinate |
| 15 | 2-phenylethyl 4-amino-3-chloro-6-(4-chloro-2-fluoro-3-methoxyphenyl)-5-fluoropicolinate |
| 16 | 4-(methoxycarbonyl)benzyl 4-amino-3-chloro-6-(4-chloro-2-fluoro-3-methoxyphenyl)-5-fluoropicolinate |
| 18 | 4-chlorobenzyl 4-amino-3-chloro-6-(4-chloro-2-fluoro-3-methoxyphenyl)-5-fluoropicolinate |

TABLE 1-continued

Structures of Compounds in Examples

| Compound Number | Structure |
|---|---|
| 19 | 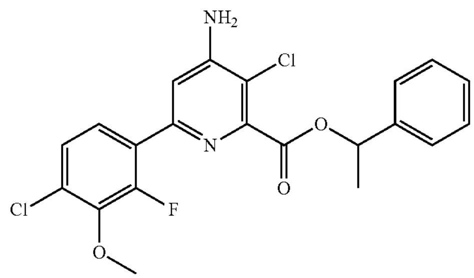 [SMILES: COc1c(Cl)ccc(-c2cc(N)c(Cl)c(C(=O)OC(C)c3ccccc3)n2)c1F] |
| 21 | 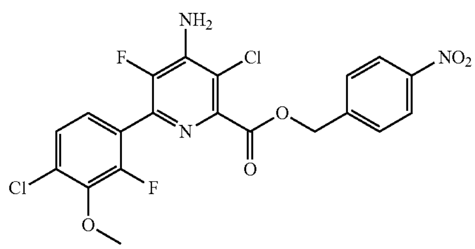 [SMILES: COc1c(Cl)ccc(-c2nc(C(=O)OCc3ccc([N+](=O)[O-])cc3)c(Cl)c(N)c2F)c1F] |
| 22 | 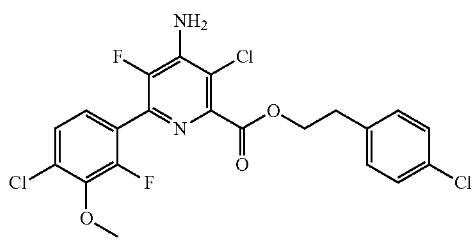 [SMILES: COc1c(Cl)ccc(-c2nc(C(=O)OCCc3ccc(Cl)cc3)c(Cl)c(N)c2F)c1F] |
| 23 | 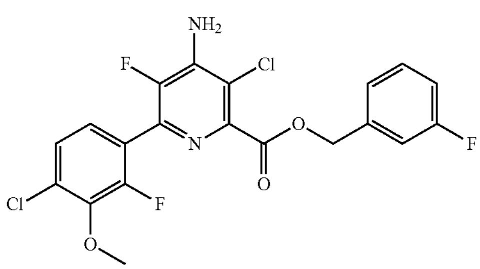 |
| 24 | 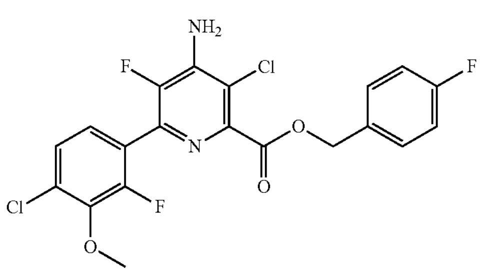 [SMILES: COc1c(Cl)ccc(-c2nc(C(=O)OCc3ccc(F)cc3)c(Cl)c(N)c2F)c1F] |
| 25 | |
| 26 | |
| 27 | |
| 28 | |
| 29 | |

TABLE 1-continued

Structures of Compounds in Examples

| Compound Number | Structure |
|---|---|
| 30 | 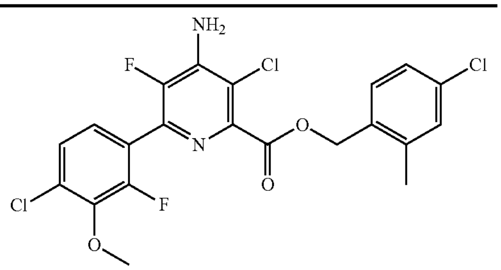 |
| 31 | 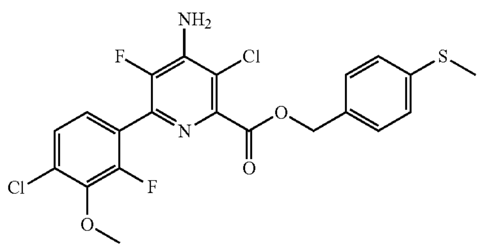 |
| 32 | 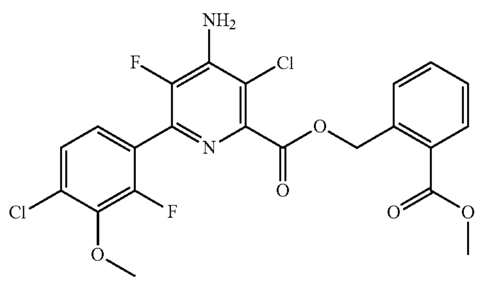 [SMILES: COC(=O)c1ccccc1COC(=O)c1nc(-c2ccc(Cl)c(OC)c2F)c(F)c(N)c1Cl] |
| 33 | 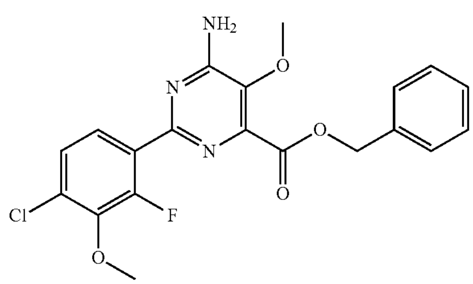 [SMILES: COc1c(N)nc(-c2ccc(Cl)c(OC)c2F)nc1C(=O)OCc1ccccc1] |
| 34 | 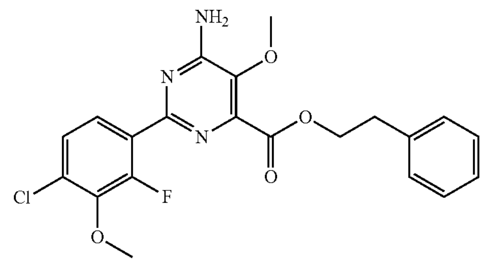 [SMILES: COc1c(N)nc(-c2ccc(Cl)c(OC)c2F)nc1C(=O)OCCc1ccccc1] |
| 37 | 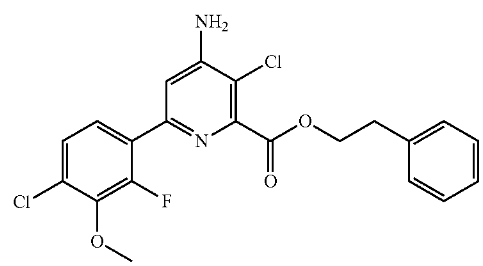 [SMILES: COc1c(Cl)ccc(-c2cc(N)c(Cl)c(C(=O)OCCc3ccccc3)n2)c1F] |
| 39 | 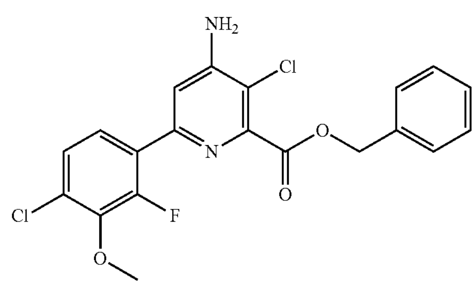 |

TABLE 2

Analytical Data for Compounds in Table 1

| Compound Number | Appearance | mp (° C.) | ESIMS m/z | $^1$H NMR (field strength, solvent) | Other NMR Data |
|---|---|---|---|---|---|
| 3 | White Solid | 139 | 453 ([M + H]$^+$) | (400 MHz, DMSO-d$_6$) δ 7.45 (dd, J = 8.5, 1.6 Hz, 1H), 7.34 (d, J = 8.0 Hz, 2H), 7.28 (dd, J = 8.5, 7.1 Hz, 1H), 7.20 (d, J = 7.9 Hz, 2H), 7.07 (s, 2H), 5.32 (s, 2H), 3.92 (d, J = 0.8 Hz, 3H), 2.30 (s, 3H) | |
| 4 | White Solid | 151 | 464 ([M + H]$^+$) | (400 MHz, DMSO-d$_6$) δ 7.92-7.84 (m, 2H), 7.65 (d, J = 8.5 Hz, 2H), 7.47 | |

TABLE 2-continued

Analytical Data for Compounds in Table 1

| Compound Number | Appearance | mp (° C.) | ESIMS m/z | ¹H NMR (field strength, solvent) | Other NMR Data |
|---|---|---|---|---|---|
| | | | | (dd, J = 8.5, 1.6 Hz, 1H), 7.30 (dd, J = 8.5, 7.1 Hz, 1H), 7.10 (s, 2H), 5.48 (s, 2H), 3.93 (d, J = 0.9 Hz, 3H) | |
| 5 | White Solid | 183-184 | 469 ([M + H]⁺), 467 ([M − H]⁻) | (400 MHz, DMSO-d₆) δ 7.43 (d, J = 8.4 Hz, 1H), 7.29-7.12 (m, 4H), 6.88 (d, J = 8.7 Hz, 2H), 4.59 (d, J = 4.4 Hz, 2H), 3.90 (s, 3H), 3.71 (s, 3H) | |
| 6 | White Solid | 118-119 | 507 ([M + H]⁺), 505 ([M − H]⁻) | (400 MHz, DMSO-d₆) δ 7.79 (d, J = 8.2 Hz, 2H), 7.68 (d, J = 8.1 Hz, 2H), 7.47 (dd, J = 8.5, 1.5 Hz, 1H), 7.31 (dd, J = 8.5, 7.1 Hz, 1H), 7.15 (s, 2H), 5.49 (s, 2H), 3.93 (d, J = 0.7 Hz, 3H) | |
| 7 | Yellow Solid | 170-175 | 449 ([M + H]⁺), 447 ([M − H]⁻) | (400 MHz, CDCl₃) δ 8.03-7.94 (m, 2H), 7.70-7.59 (m, 2H), 7.51 (dd, J = 10.6, 4.8 Hz, 2H), 7.22 (dd, J = 7.7, 1.6 Hz, 2H), 5.63 (s, 2H), 4.95 (s, 2H), 3.96 (d, J = 0.8 Hz, 3H) | |
| 8 | White Solid | 135 | 453 ([M + H]⁺), 451 ([M − H]⁻) | (400 MHz, DMSO-d₆) δ 7.50-7.38 (m, 2H), 7.33-7.18 (m, 4H), 7.13 (s, 2H), 5.39 (s, 2H), 3.92 (d, J = 0.7 Hz, 3H), 2.35 (s, 3H) | |
| 9 | White Solid | 183-184 | 474 ([M + H]⁺), 472 ([M − H]⁻) | (400 MHz, DMSO-d₆) δ 7.62 (dd, J = 7.0, 2.3 Hz, 1H), 7.57-7.37 (m, 4H), 7.30 (dd, J = 8.5, 7.1 Hz, 1H), 7.14 (s, 2H), 5.45 (s, 2H), 3.92 (s, 3H) | |
| 10 | White Solid | 135-136 | 469 ([M + H]⁺) | (400 MHz, DMSO-d₆) δ 7.46 (dd, J = 8.5, 1.5 Hz, 1H), 7.43-7.33 (m, 2H), 7.29 (dd, J = 8.5, 7.1 Hz, 1H), 7.11 (s, 2H), 7.05 (d, J = 8.0 Hz, 1H), 6.96 (td, J = 7.4, 0.9 Hz, 1H), 5.34 (s, 2H), 3.92 (d, J = 0.5 Hz, 3H), 3.81 (s, 3H) | |
| 11 | White Solid | 150 | 453 ([M + H]⁺), 451 ([M − H]⁻) | (400 MHz, DMSO-d₆) δ 7.46 (dd, J = 8.5, 1.5 Hz, 1H), 7.32-7.21 (m, 4H), 7.17 (d, J = 7.2 Hz, 1H), 7.13 (s, 2H), 5.34 (s, 2H), 3.92 (d, J = 0.7 Hz, 3H), 2.31 (s, 3H) | |
| 12 | White Solid | 147-148 | 474 ([M + H]⁺), 472 ([M − H]⁻) | (400 MHz, DMSO-d₆) δ 7.55 (s, 1H), 7.51-7.39 (m, 4H), 7.30 (dd, J = 8.5, 7.1 Hz, 1H), 7.15 (s, 2H), 5.40 (s, 2H), 3.93 (d, J = 0.7 Hz, 3H) | |
| 13 | White Solid | 164-165 | 469 ([M + H]⁺), 467 ([M − H]⁻) | (400 MHz, DMSO-d₆) δ 7.47 (dd, J = 8.5, 1.5 Hz, 1H), 7.36-7.25 (m, 2H), 7.14 (s, 2H), 7.02 (d, J = 7.4 Hz, 2H), 6.96-6.88 (m, 1H), 5.35 (s, 2H), 3.93 (d, J = 0.7 Hz, 3H), 3.74 (s, 3H) | |
| 14 | Colorless Oil | | 453 ([M + H]⁺), 451 ([M − H]⁻) | (400 MHz, DMSO-d₆) δ 7.50-7.43 (m, 3H), 7.41-7.35 (m, 2H), 7.35-7.26 (m, 2H), 7.07 (s, 2H), 6.08 (q, J = 6.5 Hz, 1H), 3.93 (d, J = 0.9 Hz, | ¹⁹F NMR (376 MHz, DMSO-d₆) δ −129.03 (d, J = 28.1 Hz), −137.77 (d, J = 28.1 |

TABLE 2-continued

Analytical Data for Compounds in Table 1

| Compound Number | Appearance | mp (° C.) | ESIMS m/z | ¹H NMR (field strength, solvent) | Other NMR Data |
|---|---|---|---|---|---|
| | | | | 3H), 1.61 (d, J = 6.6 Hz, 3H) | Hz) |
| 15 | White Solid | 84-85 | 453 ([M + H]⁺), 451 ([M − H]⁻) | (400 MHz, DMSO-d₆) δ 7.47 (dd, J = 8.5, 1.6 Hz, 1H), 7.36-7.18 (m, 6H), 7.05 (s, 2H), 4.53 (t, J = 6.8 Hz, 2H), 3.93 (d, J = 1.0 Hz, 3H), 3.02 (t, J = 6.8 Hz, 2H) | |
| 16 | White Solid | 182 | 498 ([M + H]⁺), 496 ([M − H]⁻) | (400 MHz, DMSO-d₆) δ 8.02-7.95 (m, 2H), 7.59 (d, J = 8.5 Hz, 2H), 7.46 (dd, J = 8.5, 1.6 Hz, 1H), 7.30 (dd, J = 8.5, 7.1 Hz, 1H), 7.09 (s, 2H), 5.47 (s, 2H), 3.93 (d, J = 1.0 Hz, 3H), 3.86 (s, 3H) | |
| 18 | White Solid | 100-108 | 457 ([M + H]⁺), 455 ([M − H]⁻) | (400 MHz, CDCl₃) δ 7.64 (dd, J = 8.6, 7.8 Hz, 1H), 7.44-7.32 (m, 4H), 7.22 (dd, J = 8.7, 1.8 Hz, 1H), 7.17 (d, J = 1.6 Hz, 1H), 5.40 (s, 2H), 4.85 (s, 2H), 3.96 (d, J = 0.9 Hz, 3H) | |
| 19 | White Solid | 110-113 | 435 ([M + H]⁺), 433 ([M − H]⁻) | (400 MHz, CDCl₃) δ 7.71 (dd, J = 8.6, 7.8 Hz, 1H), 7.49 (dd, J = 5.4, 3.4 Hz, 2H), 7.40-7.34 (m, 2H), 7.33-7.28 (m, 1H), 7.23 (dd, J = 8.7, 1.7 Hz, 1H), 7.18 (d, J = 1.6 Hz, 1H), 6.21 (q, J = 6.6 Hz, 1H), 4.80 (s, 2H), 3.97 (d, J = 0.8 Hz, 3H), 1.72 (d, J = 6.6 Hz, 3H) | |
| 21 | White Solid | 207-208 | 484 ([M + H]⁺), 482 ([M − H]⁻) | (400 MHz, acetone-d₆) δ 8.33-8.25 (m, 2H), 7.85-7.77 (m, 2H), 7.40 (ddd, J = 15.3, 8.5, 4.1 Hz, 2H), 6.52 (s, 1H), 5.59 (s, 2H), 3.99 (d, J = 1.1 Hz, 3H) | |
| 22 | White Solid | 107-108 | 485 ([M − H]⁻) | (400 MHz, DMSO-d₆) δ 7.48 (dd, J = 8.5, 1.6 Hz, 1H), 7.34 (s, 4H), 7.27 (dd, J = 8.5, 7.1 Hz, 1H), 7.09 (s, 2H), 4.52 (t, J = 6.6 Hz, 2H), 3.93 (d, J = 0.8 Hz, 3H), 3.01 (t, J = 6.6 Hz, 2H) | |
| 23 | White Solid | 160-161 | 457 ([M + H]⁺), 455 ([M − H]⁻) | (400 MHz, DMSO-d₆) δ 7.50-7.41 (m, 2H), 7.34-7.26 (m, 3H), 7.20 (s, 1H), 7.14 (s, 2H), 5.40 (s, 2H), 3.92 (d, J = 0.6 Hz, 3H) | |
| 24 | White Solid | 143-144 | 457 ([M + H]⁺) | (400 MHz, DMSO-d₆) δ 7.55-7.50 (m, 2H), 7.46 (dd, J = 8.5, 1.5 Hz, 1H), 7.31-7.20 (m, 3H), 7.13 (s, 2H), 5.36 (s, 2H), 3.92 (s, 3H) | |
| 25 | White Solid | 169 | 457 ([M + H]⁺), 455 ([M − H]⁻) | (400 MHz, DMSO-d₆) δ 7.57 (dt, J = 9.4, 4.7 Hz, 1H), 7.45 (ddd, J = 9.4, 4.6, 1.7 Hz, 2H), 7.26 (ddd, J = 15.6, 7.3, 2.8 Hz, 3H), 7.13 (s, 2H), 5.42 (s, 2H), 3.92 (d, J = 0.5 Hz, 3H) | |
| 26 | White Solid | 133-134 | 507 ([M + H]⁺), 505 ([M − H]⁻) | (400 MHz, DMSO-d₆) δ 7.84-7.69 (m, 3H), 7.61 (t, J = 7.5 Hz, 1H), 7.48 (dd, J = 8.5, 1.5 Hz, 1H), | |

TABLE 2-continued

Analytical Data for Compounds in Table 1

| Compound Number | Appearance | mp (° C.) | ESIMS m/z | ¹H NMR (field strength, solvent) | Other NMR Data |
|---|---|---|---|---|---|
| | | | | 7.29 (dd, J = 8.5, 7.1 Hz, 1H), 7.15 (s, 2H), 5.53 (s, 2H), 3.92 (d, J = 0.6 Hz, 3H) | |
| 27 | White Solid | 75-76 | 481 ([M + H]⁺), 479 ([M − H]⁻) | (400 MHz, DMSO-d₆) δ 7.46 (dd, J = 8.5, 1.5 Hz, 1H), 7.37 (d, J = 8.1 Hz, 2H), 7.32-7.23 (m, 3H), 7.12 (s, 2H), 5.32 (s, 2H), 3.92 (d, J = 0.7 Hz, 3H), 2.88 (dt, J = 13.7, 6.8 Hz, 1H), 1.19 (d, J = 6.9 Hz, 6H) | |
| 28 | White Solid | 142-143 | 489 ([M + H]⁺), 487 ([M − H]⁻) | (400 MHz, acetone-d₆) δ 8.06 (s, 1H), 8.00-7.90 (m, 3H), 7.65 (dd, J = 8.5, 1.7 Hz, 1H), 7.59-7.51 (m, 2H), 7.40 (ddd, J = 15.3, 8.5, 4.1 Hz, 2H), 6.49 (s, 2H), 5.61 (s, 2H), 4.00 (d, J = 1.1 Hz, 3H) | |
| 29 | White Solid | 144-145 | 497 ([M + H]⁺), 495 ([M − H]⁻) | (400 MHz, acetone-d₆) δ 8.19 (dd, J = 1.7, 1.2 Hz, 1H), 8.01 (dt, J = 7.8, 1.4 Hz, 1H), 7.79 (ddd, J = 7.7, 1.7, 1.2 Hz, 1H), 7.58 (t, J = 7.7 Hz, 1H), 7.43 (dd, J = 8.5, 1.5 Hz, 1H), 7.37 (dd, J = 8.5, 6.7 Hz, 1H), 6.50 (s, 2H), 5.53 (s, 2H), 4.00 (d, J = 1.1 Hz, 3H), 3.90 (s, 3H) | |
| 30 | White Solid | 167-168 | 485 ([M − H]⁻) | (400 MHz, acetone-d₆) δ 7.51 (d, J = 8.2 Hz, 1H), 7.43 (dd, J = 8.5, 1.6 Hz, 1H), 7.37-7.30 (m, 2H), 7.26 (dd, J = 8.1, 2.0 Hz, 1H), 6.49 (s, 2H), 5.43 (s, 2H), 4.00 (d, J = 1.1 Hz, 3H) | |
| 31 | White Solid | 145 | 485 ([M + H]⁺), 483 ([M − H]⁻) | (400 MHz, acetone-d₆) δ 7.50-7.39 (m, 3H), 7.33 (ddd, J = 8.4, 7.9, 4.4 Hz, 3H), 6.48 (s, 2H), 5.38 (s, 2H), 4.00 (d, J = 1.1 Hz, 3H) | |
| 32 | Colorless Solid | 161 | 497 ([M + H]⁺), 495 ([M − H]⁻) | (400 MHz, acetone-d₆) δ 8.02 (dd, J = 7.8, 1.3 Hz, 1H), 7.78 (dd, J = 7.8, 0.6 Hz, 1H), 7.65 (td, J = 7.6, 1.4 Hz, 1H), 7.54-7.35 (m, 3H), 6.50 (s, 1H), 5.82 (s, 2H), 4.01 (d, J = 1.1 Hz, 3H), 3.91 (s, 3H) | |
| 33 | White Solid | 145-147 | 417 ([M + H]⁺) | (400 MHz, CDCl₃) δ 7.65-7.15 (m, 9H), 5.45 (d, J = 4.1 Hz, 2H), 5.40 (s, 2H), 3.99 (d, J = 1.0 Hz, 3H), 3.81 (d, J = 7.2 Hz, 3H) | ¹⁹F NMR (376 MHz, CDCl₃) δ −129.38 (s) |
| 34 | Clear Oil | | 431 ([M + H]⁺) | (400 MHz, CDCl₃) δ 7.59 (dd, J = 8.6, 7.5 Hz, 1H), 7.35-7.15 (m, 6H), 5.63 (s, 2H), 4.63 (td, J = 7.0, 4.0 Hz, 2H), 3.98 (d, J = 0.9 Hz, 3H), 3.75 (s, 3H), 3.15-3.07 (m, 2H) | ¹⁹F NMR (376 MHz, CDCl₃) δ −129.46 (s) |
| 37 | Yellow Oil | | 435 ([M + H]⁺), 433 ([M − H]⁻) | (400 MHz, CDCl₃) δ 7.67 (dd, J = 8.6, 7.9 Hz, 1H), 7.29 (dd, J = 15.8, 3.6 Hz, 4H), 7.25-7.20 (m, 2H), 7.19 (d, J = 1.6 Hz, 1H), 4.81 (s, 2H), | |

TABLE 2-continued

Analytical Data for Compounds in Table 1

| Compound Number | Appearance | mp (° C.) | ESIMS m/z | $^1$H NMR (field strength, solvent) | Other NMR Data |
|---|---|---|---|---|---|
| 39 | White Crystals | 90-91.5 | 421 ([M + H]$^+$) | 4.62 (t, J = 7.2 Hz, 2H), 3.97 (d, J = 0.7 Hz, 3H), 3.12 (t, J = 7.1 Hz, 2H) (400 MHz, CDCl$_3$) δ 7.73-7.11 (m, 9H), 5.45 (s, 2H), 4.81 (s, 2H), 3.97 (d, J = 0.6 Hz, 3H) | |

Example 13

Evaluation of General Postemergence Herbicidal Activity

Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 84.6 square centimeters (cm$^2$). When required to ensure good germination and healthy plants, a fungicide treatment and/or other chemical or physical treatment was applied. The plants were grown for 7-31 days (d) in a greenhouse with an approximate 15 hour (h) photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

Treatments consisted of esters of compounds 33 and 39 and F and G. Compound F is methyl 6-amino-2-(4-chloro-2-fluoro-3-methoxyphenyl)-5-methoxypyrimidine-4-carboxylate; and compound G is methyl 4-amino-3-chloro-6-(4-chloro-2-fluoro-3-methoxyphenyl)picolinate. A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of a 97:3 v/v (volume/volume) mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and ¹⁄₁₆× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters (m$^2$) at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Tables 3 and 4.

TABLE 3

Activity of Herbicidal Compounds in Post-emergent Applications at Various Rates (14 Days After Application (DAA))

| Compound Number | Application Rate (g ai/ha) | Visual Injury (%) IPOHE |
|---|---|---|
| G | 35 | 65 |
| G | 17.5 | 50 |
| G | 8.75 | 40 |
| 39 | 35 | 80 |
| 39 | 17.5 | 75 |
| 39 | 8.75 | 70 |

TABLE 4

Activity of Herbicidal Compounds in Post-emergent Applications (70 g ai/ha and 14 DAA)

| Compound Number | Visual Injury (%) | | | | |
|---|---|---|---|---|---|
| | ORYSA | TRZAS | IPOHE | VIOTR | STEME |
| F | 75 | 70 | 80 | 80 | 90 |
| 33 | 30 | 45 | 100 | 100 | 100 |

IPOHE = *Ipomoea hederacea* (Morningglory, ivyleaf)
ORYSA = *Oryza sativa* (Rice)
STEME = *Stellaria media* (Chickweed, common)
TRZAS = *Triticum aestivum* (Wheat, spring)
VIOTR = *Viola tricolor* (Pansy, wild)
g ai/ha = grams active ingredient per hectare
DAA = days after application

Example 14

Evaluation of Postemergence Herbicidal Activity in Cereal Crops

Seeds of the desired test plant species were planted in Sun Gro Metro-Mix® 360 planting mixture, which typically has a pH of 6.0 to 6.8 and an organic matter content of about 30 percent, in plastic pots with a surface area of 84.6 cm$^2$. When required to ensure good germination and healthy plants, a fungicide treatment and/or other chemical or physical treatment was applied. The plants were grown for 7-36 d in a greenhouse with an approximate 14 h photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of esters of compounds 33, 34, 39, 40 and 42 and B, F, G and H. Compound B is methyl 4-amino-3-chloro-6-(4-cyclopropylphenyl)-5-fluoropicolinate; compound F is methyl 6-amino-2-(4-chloro-2-fluoro-3-methoxyphenyl)-5-methoxypyrimidine-4-carboxylate; compound G is methyl 4-amino-3-chloro-6-(4-chloro-2-fluoro-3-methoxyphenyl)picolinate; and compound H is methyl 4-amino-3-chloro-6-(4-chloro-2-fluoro-3-(1-fluoroethyl)phenyl)-5-fluoropicolinate. A weighed amount, determined by the highest rate to be tested, of each test compound was placed in a 25 mL glass vial and was dissolved in 8 mL of a 97:3 v/v mixture of acetone and DMSO to obtain concentrated stock solutions. If the test compound did not dissolve readily, the mixture was warmed and/or sonicated. The concentrated stock solutions obtained were diluted with 16 mL of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio to obtain spray solutions containing the highest application rates. Additional application rates were obtained by serial dilution of 12 mL of the high rate solution into a solution containing 4 mL of a 97:3 v/v mixture of acetone and DMSO and 8 mL of an aqueous mixture containing acetone, water, isopropyl alcohol, DMSO, Agri-dex crop oil concentrate, and Triton® X-77 surfactant in a 48.5:39.0:10.0:1.5:1.0:0.02 v/v ratio to obtain ½×, ¼×, ⅛× and ¹⁄₁₆× rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 m² at a spray height of 18 inches (43 cm) above average plant canopy height. Control plants were sprayed in the same manner with the blank.

The treated plants and control plants were placed in a greenhouse as described above and watered by sub-irrigation to prevent wash-off of the test compounds. After 20-22 d, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Tables 5-10.

TABLE 5

Activity of Herbicidal Compounds in Wheat Cropping Systems (35 g ae/ha and 21 DAA)

| Compound Number | Visual Injury (%) | |
| --- | --- | --- |
| | POLCO | SINAR |
| B | 62 | 70 |
| 42 | 95 | 93 |

TABLE 6

Activity of Herbicidal Compounds in Wheat Cropping Systems (35 g ae/ha and 21 DAA)

| Compound Number | Visual Injury (%) | | | | |
| --- | --- | --- | --- | --- | --- |
| | SINAR | KCHSC | SASKR | MATCH | POLCO |
| G | 80 | 87 | 80 | 75 | 85 |
| 39 | 95 | 95 | 90 | 95 | 95 |

TABLE 7

Activity of Herbicidal Compounds in Wheat Cropping Systems at various rates (21 DAA)

| Compound Number | Application Rate (g ae/ha) | Visual Injury (%) CIRAR |
| --- | --- | --- |
| G | 17.5 | 80 |
| G | 8.75 | 70 |
| 39 | 17.5 | 95 |
| 39 | 8.75 | 90 |

TABLE 8

Activity of Herbicidal Compounds in Wheat Cropping Systems (8.75 g ae/ha and 21 DAA)

| Compound Number | Visual Injury (%) | | |
| --- | --- | --- | --- |
| | SINAR | VERPE | PESGL |
| H | 87 | 80 | 0 |
| 40 | 98 | 95 | 65 |

TABLE 9

Activity of Herbicidal Compounds in Wheat Cropping Systems (35 g ae/ha and 21 DAA)

| Compound Number | Visual Injury (%) | |
| --- | --- | --- |
| | MATCH | AVEFA |
| F | 10 | 20 |
| 33 | 40 | 40 |
| 34 | 20 | 40 |

TABLE 10

Activity of Herbicidal Compounds in Wheat Cropping Systems (17.5 g ae/ha and 21 DAA)

| Compound Number | Visual Injury (%) | |
| --- | --- | --- |
| | LOLMU | SETVI |
| F | 60 | 85 |
| 33 | 80 | 93 |
| 34 | 70 | 80 |

AVEFA = *Avena fatua* (Oat, wild)
CIRAR = *Cirsium arvense* (Thistle, Canada)
KCHSC = *Kochia scoparia* (Kochia)
LOLMU = *Lolium multiflorum* (Ryegrass, Italian)
MATCH = *Matricaria chamomilla* (Mayweed, wild)
PESGL = *Pennisetum glaucum* (Foxtail, yellow)
POLCO = *Polygonum convolvulus* (Buckwheat, wild)
SASKR = *Salsola kali* (Thistle, Russian)
SETVI = *Setaria viridis* (Foxtail, green)
SINAR = *Brassica sinapis* (Mustard, wild)
VERPE = *Veronica persica* (Speedwell, birdseye)
g ae/ha = grams acid equivalent per hectare
DAA = days after application

Example 15

Evaluation of Postemergence Herbicidal Activity in Pastures

Seeds of the desired test plant species were planted in Sun Gro Metro-Mix® 360 planting mixture, which typically has a pH of 6.0 to 6.8 and an organic matter content of about 30 percent, in plastic pots with a surface area of 139.7 cm². When required to ensure good germination and healthy plants, a fungicide treatment and/or other chemical or physical treatment was applied. The plants were grown with an approximate 14 h photoperiod which was maintained at about 24° C. during the day and 21° C. during the night. Nutrients and water were added on a regular basis and supplemental lighting was provided with overhead metal halide 1000-Watt lamps as necessary. The plants were employed for testing when they reached the four or six true leaf stage, depending on species.

Treatments consisted of esters of compounds 39 and G. Compound G is methyl 4-amino-3-chloro-6-(4-chloro-2-fluoro-3-methoxyphenyl)picolinate. A weighed amount, determined by the highest rate to be tested, of each test compound was placed in a 25 mL glass vial and was dissolved in 8 mL of a 97:3 v/v mixture of acetone and DMSO to obtain concentrated stock solutions. If the test compound did not dissolve readily, the mixture was warmed and/or sonicated. The concentrated stock solutions obtained were diluted with 16 mL of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio to obtain spray solutions containing the highest application rates. Additional application rates were obtained by serial dilution of 12 mL of the high rate solution into a solution containing 4 mL of a 97:3 v/v mixture of acetone and DMSO and 8 mL of an aqueous mixture containing acetone, water, isopropyl alcohol, DMSO, Agri-dex crop oil concentrate, and Triton® X-77 surfactant in a 48.5:39.0:10.0:1.5:1.0:0.02 v/v ratio to obtain ½×, ¼×, ⅛× and 1/16× rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 m² at a spray height of 18 inches (43 cm) above average plant canopy height. Control plants were sprayed in the same manner with the blank.

The treated plants and control plants were placed in a greenhouse as described above and watered by sub-irrigation to prevent wash-off of the test compounds. After 35 d, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Tables 11 and 12.

TABLE 11

Activity of Herbicidal Compounds in Pasture Cropping Systems at various rates (35 DAA)

| Compound Number | Application Rate (g ae/ha) | Visual Injury (%) CIRAR |
|---|---|---|
| G | 35 | 60 |
| G | 17.5 | 40 |
| 39 | 35 | 95 |
| 39 | 17.5 | 100 |

TABLE 12

Activity of Herbicidal Compounds in Pasture Cropping Systems at Various Rates (35 DAA)

| Compound Number | Application Rate (g ae/ha) | Visual Injury (%) SOOSS |
|---|---|---|
| G | 140 | 50 |
| G | 70 | 30 |
| 39 | 140 | 100 |
| 39 | 70 | 85 |

CIRAR = *Cirsium arvense* (Thistle, Canada)
SOOSS = *Solidago* L. spec (Goldenrod)
g ae/ha = g acid equivalent per hectare
DAA = days after application

Example 16

Evaluation of Postemergence Foliar-Applied Herbicidal Activity in Direct Seeded Rice Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 cm². When required to ensure good germination and healthy plants, a fungicide treatment and/or other chemical or physical treatment was applied. The plants were grown for 10-17 d in a greenhouse with an approximate 14-h photoperiod which was maintained at about 29° C. during the day and 26° C. during the night. Nutrients and water were added on a regular basis and supplemental lighting was provided with overhead metal halide 1000-Watt lamps as necessary. The plants were employed for testing when they reached the second or third true leaf stage.

Treatments consisted of esters of compounds 1-4, 6-8, 10, 11, 13-16, 20-31, 35, 38, 41 and 42 and A-E. Compound A is methyl 4-amino-3-chloro-6-(4-chloro-3-ethoxy-2-fluorophenyl)-5-fluoropicolinate; compound B is methyl 4-amino-3-chloro-6-(4-cyclopropylphenyl)-5-fluoropicolinate; compound C is methyl 4-amino-3-chloro-6-(2,4-dichloro-3-methoxyphenyl)picolinate; compound D is methyl 6-amino-2-(4-chloro-2-fluoro-3-methoxyphenyl)-5-vinylpyrimidine-4-carboxylate; and compound E is methyl 4-amino-3-chloro-6-(4-chloro-2-fluoro-3-methoxyphenyl)-5-fluoropicolinate. Weighed amounts of technical grade compounds were placed in 25 mL glass vials and dissolved in a volume of 97:3 v/v acetone-DMSO to obtain 12× stock solutions. If the test compound did not dissolve readily, the mixture was warmed and/or sonicated. The concentrated stock solutions were added to the spray solutions so that the final acetone and DMSO concentrations were 16.2% and 0.5%, respectively. Spray solutions were diluted to the appropriate final concentrations with the addition of 10 mL of an aqueous mixture of 1.5% (v/v) Agri-dex crop oil concentrate. Generally, multiple concentrations of spray solutions were formulated and tested utilizing the same stock solution. The final spray solutions contained 1.25% (v/v) Agridex crop oil concentrate. Compound requirements are based upon a 12 mL application volume at a rate of 187 L/ha. Spray solutions were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy height. Control plants were sprayed in the same manner with the solvent blank.

The treated plants and control plants were placed in a greenhouse as described above and watered by sub-irrigation to prevent wash-off of the test compounds. After 3 weeks, the condition of the test plants, compared with that of the untreated plants, was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the data gathered can be used to calculate $GR_{50}$ and $GR_{80}$ values, which are defined as growth reduction factors that correspond to the effective dose of herbicide required to kill or control 50 percent or 80 percent, respectively, of a target plant.

Some of the application rates and ratios employed, plant species tested, and results are given in Tables 13-18.

TABLE 13

Activity of Herbicidal Compounds in Rice Cropping Systems (17.5 g ae/ha and 21 DAA; visual injury may represent data gathered in multiple trials)

| Compound | Visual Injury (%) | | | | | | |
|---|---|---|---|---|---|---|---|
| Number | ECHCG | ECHCO | AESSE | SEBEX | CYPES | CYPIR | SCPJU |
| A | 60 | 50 | 0 | 20 | 60 | 80 | 20 |
| 41 | 95 | 95 | 100 | 99 | 100 | 100 | 90 |

TABLE 14

Activity of Herbicidal Compounds in Rice Cropping Systems (8.75 g ae/ha and 21 DAA; visual injury may represent data gathered in multiple trials)

| Compound | Visual Injury (%) | |
|---|---|---|
| Number | ECHCO | CYPIR |
| B | 50 | 60 |
| 42 | 85 | 100 |

TABLE 15

Activity of Herbicidal Compounds in Rice Cropping Systems (8.75 g ae/ha and 21 DAA; visual injury may represent data gathered in multiple trials)

| Compound | Visual Injury (%) | | | |
|---|---|---|---|---|
| Number | ECHCO | BRAPP | CYPDI | SCPJU |
| C | 84 | 74 | 96 | 90 |
| 38 | 90 | 90 | 100 | 100 |

TABLE 16

Activity of Herbicidal Compounds in Rice Cropping Systems (8.75 g ae/ha and 21 DAA; visual injury may represent data gathered in multiple trials)

| Compound | Visual Injury (%) | |
|---|---|---|
| Number | ECHCG | ECHCO |
| D | 87 | 79 |
| 35 | 95 | 90 |

TABLE 17

Activity of Herbicidal Compounds in Rice Cropping Systems (8.75 g ae/ha and 21 DAA; visual injury may represent data gathered in multiple trials)

| Compound | Visual Injury (%) | |
|---|---|---|
| Number | CYPDI | SCPJU |
| E | 89 | 61 |
| 1 | 100 | 93 |
| 8 | 99 | 99 |
| 25 | 100 | 100 |
| 26 | 100 | 100 |
| 10 | 100 | 91 |
| 11 | 99 | 97 |
| 23 | 100 | 100 |

TABLE 17-continued

Activity of Herbicidal Compounds in Rice Cropping Systems (8.75 g ae/ha and 21 DAA; visual injury may represent data gathered in multiple trials)

| Compound | Visual Injury (%) | |
|---|---|---|
| Number | CYPDI | SCPJU |
| 13 | 95 | 80 |
| 29 | 100 | 100 |
| 3 | 100 | 99 |
| 2 | 100 | 100 |
| 24 | 100 | 100 |
| 6 | 100 | 100 |
| 16 | 94 | 85 |
| 4 | 80 | 80 |
| 20 | 100 | 100 |
| 21 | 100 | 100 |
| 27 | 100 | 100 |
| 31 | 100 | 100 |
| 30 | 99 | 0 |
| 15 | 100 | 90 |
| 22 | 100 | 90 |
| 28 | 100 | 100 |
| 7 | 70 | 60 |
| 14 | 95 | 50 |

TABLE 18

Growth Reduction Calculations for
Compounds in Rice Cropping Systems

| Species | Compound Number | $GR_{50}$ | $GR_{80}$ g ae/ha | $GR_{90}$ |
|---|---|---|---|---|
| ECHCG | E | 3.7 | 17.1 | 38.1 |
|  | 1 | <4.38 | <4.38 | 6.1 |
| POLPY | E | 30.7 | >70 | >70 |
|  | 1 | <8.75 | 19.7 | 46.7 |
| BRAPP | E | <4.38 | 22.7 | 84.3 |
|  | 1 | <4.38 | 9.9 | 26.0 |
| ECHCO | E | <4.38 | 14.6 | 55.6 |
|  | 1 | 2.4 | 7.8 | 14.4 |

AESSE = *Aeschynomene sensitive* SW./L. (sensitive jointvetch)
BRAPP = *Brachiaria platyphylla* (GRISEB.) NASH (broadleaf signalgrass)
CYPDI = *Cyperus difformis* L. (small-flower flatsedge)
CYPES = *Cyperus esculentus* L. (yellow nutsedge)
CYPIR = *Cyperus iria* L. (rice flatsedge)
ECHCG = *Echinochloa crus-galli* (L.) P.BEAUV. (barnyardgrass)
ECHCO = *Echinochloa colonum* (L.) LINK (junglerice)
POLPY = *Polygonum pensylvanicum* L. (Pennsylvania smartweed)
SCPJU = *Scirpus juncoides* ROXB. (Japanese bulrush)
SEBEX = *Sesbania exaltata* (RAF.) CORY/RYDB. (hemp sesbania)
g ae/ha = gram acid equivalent per hectare
DAA = days after application
$GR_{50}$ = concentration of compound needed to reduce the growth of a plant by 50% relative to untreated plant
$GR_{80}$ = concentration of compound needed to reduce the growth of a plant by 80% relative to untreated plant
$GR_{90}$ = concentration of compound needed to reduce the growth of a plant by 90% relative to untreated plant Example 17

Evaluation of In-Water Applied Herbicidal Activity
in Transplanted Paddy Rice

Weed seeds or nutlets of the desired test plant species were planted in puddled soil (mud) prepared by mixing a non-sterilized mineral soil (28 percent silt, 18 percent clay, and 54 percent sand, with a pH of about 7.3 to 7.8 and an organic matter content of about 1.0 percent) and water at a ratio of 100 kilograms (kg) of soil to 19 liters (L) of water. The prepared mud was dispensed in 250 mL aliquots into 480 mL non-perforated plastic pots with a surface area of 91.6 cm² leaving a headspace of 3 cm in each pot. Rice seeds were planted in Sun Gro MetroMix 306 planting mixture, which typically has a pH of 6.0 to 6.8 and an organic matter content of about 30 percent, in plastic plug trays. Seedlings at the second or third leaf stage of growth were transplanted into 650 mL of mud contained in 960 mL non-perforated plastic pots with a surface area of 91.6 cm² four days prior to herbicide application. The paddy was created by filling the 3 cm headspace of the pots with water. When required to ensure good germination and healthy plants, a fungicide treatment and/or other chemical or physical treatment was applied. The plants were grown for 4-14 d in a greenhouse with an approximate 14-h photoperiod which was maintained at about 29° C. during the day and 26° C. during the night. Nutrients were added as Osmocote (17:6:10, Nitrogen:Phosphorus:Potassium (N:P:K)+minor nutrients) at 2 grams (g) per cup. Water was added on a regular basis to maintain the paddy flood, and supplemental lighting was provided with overhead metal halide 1000-Watt lamps as necessary. The plants were employed for testing when they reached the second or third true leaf stage.

Treatments consisted of esters of compounds 1-4, 6-33, 35-39, 41 and 42 and A-G. Compound A is methyl 4-amino-3-chloro-6-(4-chloro-3-ethoxy-2-fluorophenyl)-5-fluoropicolinate; compound B is methyl 4-amino-3-chloro-6-(4-cyclopropylphenyl)-5-fluoropicolinate; compound C is methyl 4-amino-3-chloro-6-(2,4-dichloro-3-methoxyphenyl)picolinate; compound D is methyl 6-amino-2-(4-chloro-2-fluoro-3-methoxyphenyl)-5-vinylpyrimidine-4-carboxylate; compound E is methyl 4-amino-3-chloro-6-(4-chloro-2-fluoro-3-methoxyphenyl)-5-fluoropicolinate; compound F is methyl 6-amino-2-(4-chloro-2-fluoro-3-methoxyphenyl)-5-methoxypyrimidine-4-carboxylate; and compound G is methyl 4-amino-3-chloro-6-(4-chloro-2-fluoro-3-methoxyphenyl) picolinate. Weighed amounts of technical grade compounds were placed in individual 120 mL glass vials and were dissolved in 20 mL of acetone to obtain concentrated stock solutions. If the test compound did not dissolve readily, the mixture was warmed and/or sonicated. The concentrated stock solutions obtained were diluted with 20 mL of an aqueous mixture containing 2.5% Agri-dex crop oil concentrate (v/v). The final application solutions contained 1.25% (v/v) Agri-dex crop oil concentrate. Generally, multiple concentrations were tested utilizing the same stock solution. Applications were made by injecting an appropriate amount of the application solution into the aqueous layer of the paddy. Control plants were treated in the same manner with the solvent blank.

The treated plants and control plants were placed in a greenhouse as described above and water was added as needed to maintain a paddy flood. After 3 weeks the condition of the test plants, compared with that of the untreated plants, was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the data gathered can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Tables 19-28.

TABLE 19

Activity of Herbicidal Compounds in Rice Cropping
Systems (35 g ae/ha and 21 DAA; visual injury may
represent data gathered in multiple trials)

| Compound Number | Visual Injury (%) | |
|---|---|---|
| | ECHCG | SCPJU |
| A | 40 | 60 |
| 41 | 95 | 100 |

TABLE 20

Activity of Herbicidal Compounds in Rice Cropping
Systems (17.5 g ae/ha and 21 DAA; visual injury
may represent data gathered in multiple trials)

| Compound Number | Visual Injury (%) ECHCG |
|---|---|
| B | 10 |
| 42 | 70 |

TABLE 21

Activity of Herbicidal Compounds in Rice Cropping Systems (35 g ae/ha and 21 DAA; visual injury may represent data gathered in multiple trials)

| Compound Number | Visual Injury (%) ECHCG | Visual Injury (%) SCPJU |
|---|---|---|
| F | 0 | 50 |
| 33 | 40 | 100 |

TABLE 22

Activity of Herbicidal Compounds in Rice Cropping Systems (35 g ae/ha and 21 DAA; visual injury may represent data gathered in multiple trials)

| Compound Number | Visual Injury (%) ECHCG | Visual Injury (%) SCPJU |
|---|---|---|
| C | 36 | 83 |
| 38 | 99 | 100 |

TABLE 23

Activity of Herbicidal Compounds in Rice Cropping Systems (35 g ae/ha and 21 DAA; visual injury may represent data gathered in multiple trials)

| Compound Number | Visual Injury (%) ECHCG |
|---|---|
| D | 54 |
| 35 | 76 |

TABLE 24

Activity of Herbicidal Compounds in Rice Cropping Systems (35 g ae/ha and 21 DAA; visual injury may represent data gathered in multiple trials)

| Compound Number | Visual Injury (%) FIMMI |
|---|---|
| G | 61 |
| 39 | 100 |
| 36 | 100 |

TABLE 25

Activity of Herbicidal Compounds in Rice Cropping Systems (35 g ae/ha and 21 DAA; visual injury may represent data gathered in multiple trials)

| Compound Number | Visual Injury (%) CYPRO |
|---|---|
| G | 47 |
| 39 | 80 |
| 17 | 100 |

TABLE 26

Activity of Herbicidal Compounds in Rice Cropping Systems (35 g ae/ha and 21 DAA; visual injury may represent data gathered in multiple trials)

| Compound Number | Visual Injury (%) ECHCG |
|---|---|
| G | 74 |
| 39 | 100 |
| 18 | 100 |
| 17 | 98 |
| 19 | 90 |
| 37 | 98 |

TABLE 27

Activity of Herbicidal Compounds in Rice Cropping Systems (17.5 g ae/ha and 21 DAA; visual injury may represent data gathered in multiple trials)

| Compound Number | Visual Injury (%) ECHCG | Visual Injury (%) SCPJU |
|---|---|---|
| E | 26 | 75 |
| 1 | 87 | 99 |
| 8 | 100 | 100 |
| 9 | 100 | 100 |
| 25 | 10 | 90 |
| 26 | 20 | 100 |
| 10 | 70 | 100 |
| 32 | 60 | 100 |
| 11 | 97 | 99 |
| 12 | 100 | 100 |
| 23 | 60 | 95 |
| 13 | 98 | 98 |
| 29 | 10 | 60 |
| 3 | 78 | 99 |
| 2 | 97 | 99 |
| 24 | 70 | 100 |
| 6 | 60 | 95 |
| 16 | 90 | 99 |
| 31 | 50 | 85 |
| 20 | 50 | 0 |
| 27 | 10 | 80 |
| 21 | 10 | 80 |
| 4 | 95 | 95 |
| 30 | 50 | 85 |
| 14 | 10 | 70 |
| 15 | 30 | 70 |
| 22 | 0 | 40 |
| 28 | 10 | 50 |
| 7 | 80 | 90 |

TABLE 28

Growth Reduction Calculations for Compounds in Rice Cropping Systems

| Species | Compound Number | $GR_{50}$ | $GR_{80}$ g ae/ha | $GR_{90}$ |
|---|---|---|---|---|
| ECHCG | E | 33.2 | 58.5 | 78.7 |
|  | 1 | 10.9 | 21.8 | 31.2 |
| SCPJU | E | 9.6 | 20.0 | 29.5 |
|  | 1 | <8.75 | 4.4 | 10.8 |
| LEFCH | E | 59.9 | 99.4 | 130.0 |
|  | 1 | 50.4 | 78.6 | 99.1 |

TABLE 28-continued

Growth Reduction Calculations for
Compounds in Rice Cropping Systems

| Species | Compound Number | $GR_{50}$ | $GR_{80}$ | $GR_{90}$ |
|---------|-----------------|-----------|-----------|-----------|
|         |                 | g ae/ha   |           |           |
| FIMMI   | E               | 14.4      | 21.7      | 26.8      |
|         | 1               | <17.5     | <17.5     | <17.5     |

CYPRO = *Cyperus rotundus* L. (purple nutsedge)
ECHCG = *Echinochloa crus-galli* (L.) P.BEAUV. (barnyardgrass)
FIMMI = *Fimbristylis miliacea* (L.) VAHL (globe fringerush)
LEFCH = *Leptochloa chinensis* (L.) NEES (Chinese sprangletop)
SCPJU = *Scirpus juncoides* ROXB. (Japanese bulrush)
g ae/ha = gram acid equivalent per hectare
DAA = days after application
$GR_{50}$ = concentration of compound needed to reduce the growth of a plant by 50% relative to untreated plant
$GR_{80}$ = concentration of compound needed to reduce the growth of a plant by 80% relative to untreated plant
$GR_{90}$ = concentration of compound needed to reduce the growth of a plant by 90% relative to untreated plant

What is claimed is:

1. A compound of Formula IB:

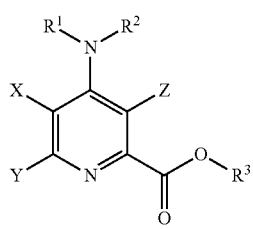

IB wherein

X represents H or F;

Y represents halogen, $C_1$-$C_8$ alkyl, $C_3$-$C_6$ cycloalkyl, or phenyl substituted with 1-4 substituents independently selected from halogen, $C_1$-$C_3$ alkyl, $C_3$-$C_6$ cycloalkyl, $C_1$-$C_3$ alkoxy, $C_1$-$C_3$ haloalkyl, $C_1$-$C_3$ haloalkoxy, cyano, nitro, $NR^1R^2$, or where two adjacent substituents are taken together as —O(CH$_2$)$_n$O— or —O(CH$_2$)$_n$— wherein n=1 or 2;

Z represents halogen or $C_2$-$C_4$ alkenyl;

$R^1$ and $R^2$ independently represent H, $C_1$-$C_6$ alkyl, or $C_1$-$C_6$ acyl;

$R^3$ represents unsubstituted or substituted $C_7$-$C_{11}$ arylalkyl.

2. The compound of claim 1 in which X represents H.

3. The compound of claim 1 in which X represents F.

4. The compound of claim 1 in which Y represents substituted phenyl.

5. The compound of claim 1 in which Z represents Cl.

6. The compound of claim 1 in which $R^1$ and $R^2$ represent H.

7. The compound of claim 1 in which $R^3$ represents a benzyl.

8. The compound of claim 1 in which $R^3$ represents an unsubstituted or ortho-, meta- or para-monosubstituted benzyl.

9. An herbicidal composition comprising an herbicidally effective amount of a compound of Formula IB, according to claim 1, in a mixture with an agriculturally acceptable adjuvant or carrier.

10. A method of controlling undesirable vegetation which comprises contacting the vegetation via foliar or water application or the locus thereof with or applying to the soil or water to prevent the emergence of vegetation an herbicidally effective amount of a compound of Formula IB, according to claim 1.

11. A method for the selective postemergent control of undesirable vegetation in the presence of rice, wheat or forage which comprises applying to said undesirable vegetation an herbicidally effective amount of a compound of Formula IB, according to claim 1, or an herbicidal composition thereof.

* * * * *